United States Patent [19]

Shiraishi et al.

[11] Patent Number: 5,576,829
[45] Date of Patent: Nov. 19, 1996

[54] METHOD AND APPARATUS FOR INSPECTING A PHASE-SHIFTED MASK

[75] Inventors: Naomasa Shiraishi; Nobutaka Magome, both of Kanagawa, Japan

[73] Assignee: Nikon Corporation, Tokyo, Japan

[21] Appl. No.: 430,266

[22] Filed: Apr. 28, 1995

Related U.S. Application Data

[63] Continuation of Ser. No. 286,804, Aug. 5, 1994, abandoned, which is a continuation of Ser. No. 32,430, Mar. 15, 1993, abandoned, which is a continuation of Ser. No. 773,350, Oct. 7, 1991, abandoned.

[30] Foreign Application Priority Data

| Oct. 8, 1990 | [JP] | Japan | 2-270213 |
| Nov. 16, 1990 | [JP] | Japan | 2-308582 |
| Nov. 16, 1990 | [JP] | Japan | 2-308583 |

[51] Int. Cl.$^6$ ............................................. G01B 9/02
[52] U.S. Cl. ................................... 356/354; 356/432
[58] Field of Search ................................ 356/354, 360, 356/355, 357, 432, 443, 389, 390, 394, 399, 237

[56] References Cited

U.S. PATENT DOCUMENTS

| 4,376,584 | 3/1983 | Hart et al. | 356/394 |
| 4,397,558 | 8/1983 | Hill et al. | 356/354 |
| 4,623,256 | 10/1986 | Ikenaga et al. | 356/394 |
| 4,718,767 | 1/1988 | Hazama | 356/389 |

*Primary Examiner*—Samuel A. Turner
*Attorney, Agent, or Firm*—Michael N. Meller

[57] ABSTRACT

A system for inspecting a phase-shifted photolithographic mask. This inspection system includes an illumination optical system for illuminating a mask, an imaging optical system for focusing an image of a pattern to be inspected on the mask, and detecting means for detecting the image of the inspection pattern whereby in accordance with one form, the amount of phase shift ($\pi+\delta$) is determined in accordance with the light quantity ratio between the images of phase-shifter deposited portions and phase-shifter non-deposited portions of the inspection pattern in a defocus condition. In accordance with another form, the direction of incidnece of an illuminating light on the mask is changed in such a manner that of the light transmitted through the inspection pattern the other beams than the 0-order diffracted beam and either one of the ±first-order diffracted beams are intercepted at a Fourier transform plane within the imageing optical system or alternatively the 0-order diffracted beam and either one of the ±first-order diffracted beams are passed through the Fourier transform plane within the imaging optical system at positions which are symmetric with the optical axis of the imaging optical system, and the amount of phase shift ($\pi+\delta$) of the phase shifters is determined in accordance with the amount of shift ($\Delta x$) within the imaging plane of the pattern image (interference pattern) detected.

29 Claims, 14 Drawing Sheets

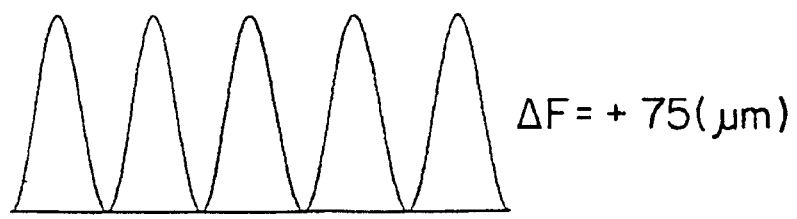
FIG.7a  ΔF = + 75 (μm)
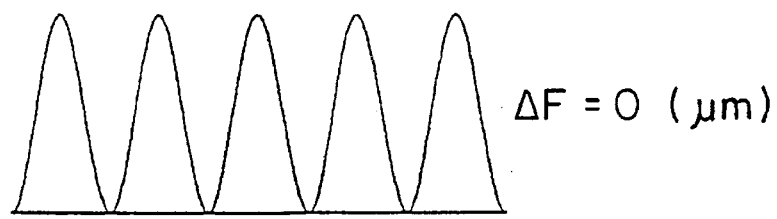
FIG.7b  ΔF = 0 (μm)
FIG.7c  ΔF = - 75 (μm)
SHIFT ANGLE = 180°

ΔF = +75 (μm)

ΔF = +75 (μm)

ΔF = 0 (μm)

ΔF = 0 (μm)

ΔF = -75 (μm)

SHIFT ANGLE = 170°

ΔF = -75 (μm)

SHIFT ANGLE = 190°

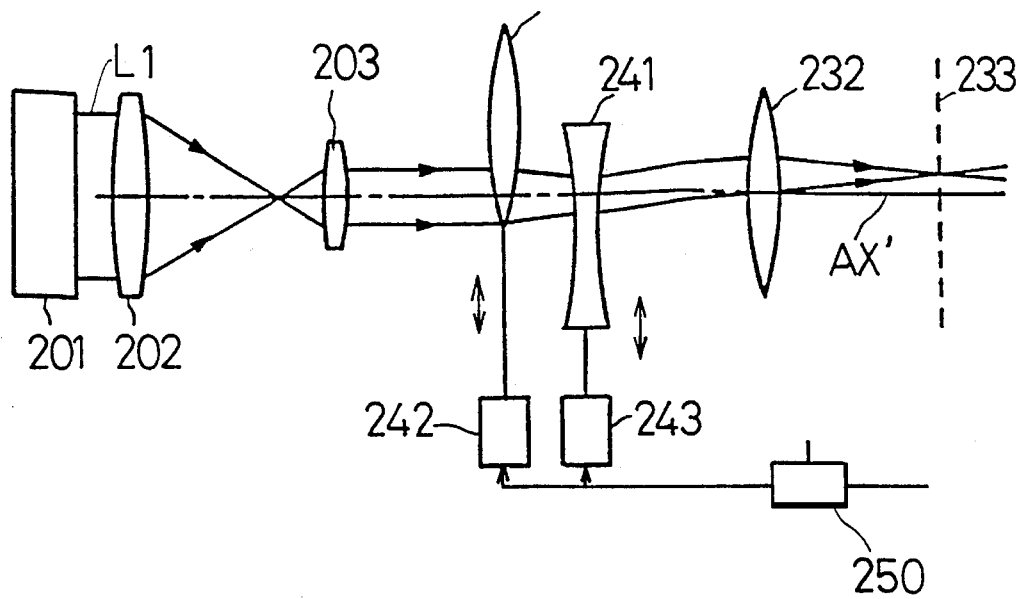
F I G. 24
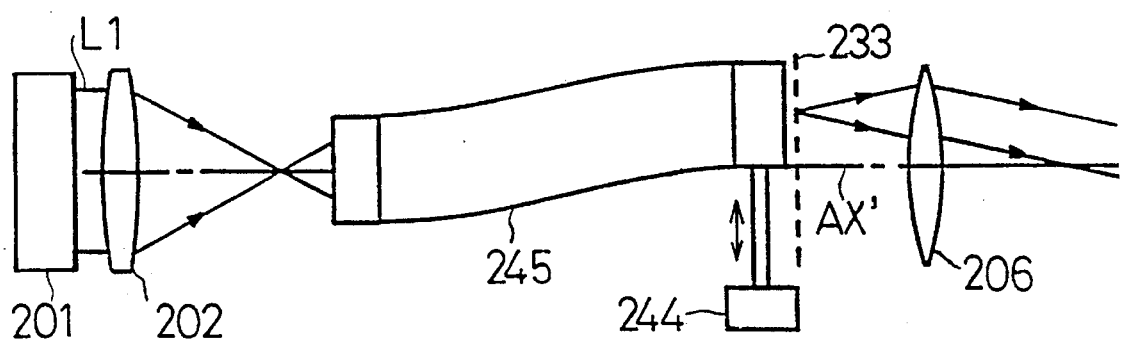
F I G. 25

METHOD AND APPARATUS FOR INSPECTING A PHASE-SHIFTED MASK

This application is a continuation of application Ser. No. 08/286,804, filed Aug. 5, 1994, which is a continuation of application Ser. No. 08/032,430, filed Mar. 15, 1993, which is a continuation of application Ser. No. 07/773,350, filed Oct. 7, 1991, now all abandoned.

BACKGROUND OF THE INVENTION

1. Field of the Invention

The present invention relates to an apparatus for inspecting a photomask (reticle) which is used as a photographic plate for the transferring or printing of a semiconductor circuit pattern, and more particularly the invention relates to a technique of measuring the amount of phase shift in a phase-shifted mask in which a plurality of phase shifters (transparent thin films) for changing the phase of transmitted light are additionally attached to its specified portions.

2. Description of the Prior Art

A mask used as a photographic plate when projecting, exposing and transferring a semiconductor circuit pattern onto the photoresist on the surface of a wafer is generally so constructed that it is made by forming a light shielding pattern of a metal such as chromium on a substrate of glass such as silica. However, such mask of the general construction is disadvantageous in that if a finer circuit pattern is used, it is impossible to ensure a satisfactory contrast for a projected image due to the diffraction of light and the interference phenomenon. Thus, recently a variety of phase-shifted masks have been proposed in which dielectric thin films, called as phase shifters, are deposited at specified locations of a mask pattern to partially change the phase of transmitted light and enhance the contrast of an image. The refractive index and film thickness of the phase shifters are designed in such a manner that a specific phase difference is produced between the light transmitted through the phase-shifter deposited portion and the light transmitted through the non-deposited portion without phase shifter under the exposure light wavelength used in the photolithography.

With such phase-shifted mask, it is important to accurately control the phase thus making it necessary to inspect the amount of phase shift caused by the phase shifters in addition to the presence of damages in the light shielding pattern and it has been the practice in the past to determine the amount of phase shift by use of a thickness gage such as an ellipsometer.

However, the ellipsometer heretofore used for the inspection of a phase-shifted mask performs the film thickness measurement by making use of the multiple reflection from the boundary surface between the mask substrate and phase shifters and the boundary surface between the phase shifters and air and therefore the measurement cannot be performed if the substrate and the phase shifters are equal in refractive index. On the other hand, the exposure light wavelength has been shortened along with the production of finer semiconductor circuit patterns so that in the future it is expected that the far ultraviolet radiation becomes the main current for the radiation source lights. While the number of materials having high transmittances for the ultraviolet radiation is not large and it is conceivable that both the mask substrate and the phase shifters will be made of silica glass, in this case the refractive indices of the two become equal and therefore the measurement of the film thickness of the phase shifters or the amount of phase shift cannot be performed by making use of the ellipsometer.

SUMMARY OF THE INVENTION

The present invention has been made in view of these circumstances and it is the primary object of the present invention to provide a method and apparatus for inspecting a phase-shifted mask capable of accurately measuring the amount of phase shift due to phase shifters (the film thickness of the phase shifters).

In accordance with the present invention there is provided a phase-shifted mask inspection method comprising the steps of: illuminating a mask and projecting onto a given imaging position an image formed by the light passed through the phase-shifter deposited portions of the mask and the light passed through the phase-shifter non-deposited portions of the mask; and calculating the phase difference between the light passed through the phase-shifter deposited portions and the light passed through the phase-shifter non-deposited portions at a position relatively moved from the imaging position of the mask in the optical axis direction in accordance with first information corresponding to the light quantities at the positions corresponding to the phase-shifter deposited portions and second information corresponding to the light quantities at the positions corresponding to the phase-shifter non-deposited portions within the image of the pattern to be inspected.

Also, in accordance with a first aspect of the present invention there is provided an inspection apparatus for performing the above-mentioned inspection method which comprises an illumination optical system for illuminating a mask, an imaging optical system for projecting onto a given imaging position an image formed by the light passed through phase-shifter deposited portions and the light passed through phase-shifter non-deposited portions; detecting means for detecting first information corresponding to the light quantities at the positions corresponding to the phase-shifter deposited portions and second information corresponding to the light quantities at the positions corresponding to the phase-shifter non-deposited portions within the image of the pattern to be inspected; and moving means for relatively moving the imaging position of the imaging optical system and the detecting means a given amount in the direction of the optical axis.

In accordance with the above-described inspection method and apparatus, objects to be inspected include for example a pattern in which the line patterns (deposited portions) of the phase shifters designed to produce for example an optical pass difference of λ/2 or a phase difference of 180° at the exposure light wavelength and the line patterns (non-deposited portions) of the phase-shifter non-deposited portions or the exposed or bare mask portions are arranged alternately or a so-called 1:1 line and space pattern in which the deposited portions and the non-deposited portions are alternately arranged each so as to be interposed between light shielding portions of chromium or the like. Then, it is constructed so that such pattern is projected onto the detector through then optical system and the light quantity distribution of the projected image near to the imaging position is measured. At this time, if the measurement is effected at a position slightly shifted from the imaging position in the direction of the optical axis of the optical system, the difference between the light quantity from the phase-shifter deposited portions and the light quantity from the phase-shifter non-deposited portions is detected. In other words, the light quantity ratio is no longer 1:1. This light quantity difference is a quantity determined by the amount of positional shift of the detector in the optical axis direction, the error ($\delta$) in the amount of phase shift due to the phase shifters and the pattern size (the line width, etc.). Therefore, if the pattern size is known and the amount of positional shift of the detector in the optical axis direction and the light quantity difference (the light quantity ratio) are measured, the error ($\delta$) in the amount of phase shift due to the phase shifters can be determined accurately so that the phase-shifted mask can be inspected without any inconvenience even if the materials of the mask substrate and the phase shifters are of the same kind. In addition, if the light quantities are measured by the detector set at two or more positions in the optical axis direction thereby averaging the measured results, it is possible to effect the measurement with greater accuracy. It is to be noted that where the line/space ratio of the line and space pattern or the pattern to be inspected is not 1:1, the previously-mentioned method can be applied by preliminarily compensating the light quantity ratio.

In accordance with a second aspect of the present invention, there is provided an inspection apparatus comprising an illumination optical system; an imaging optical system for focusing on a given imaging position a pattern image of the mask produced by the illuminating light from the illumination optical system; light shielding means arranged at or near the Fourier transform plane within the imaging optical system whereby of the light beams transmitted through the mask pattern to be inspected the light beams other than the 0-order diffracted beam and the ±first-order diffracted beams are blocked and either one of the ±first-order diffracted beams is blocked; and pattern detecting means for photoelectrically detecting the pattern image of the mask formed by the imaging optical system.

The inspecting apparatus according to the second aspect is constructed so that of the light beams transmitted through the pattern to be inspected the light beams other than the 0-order diffracted beam and either one of the ±first-order diffracted beams are blocked at substantially the Fourier transform plane within the imaging optical system and a pattern image (interference pattern) produced by the two light beams including the 0-order diffracted beam and either one of the ±first-order diffracted beams is detected at the imaging position. Where the pattern to be inspected is a line and space pattern, the interference pattern resulting from the interference of the two light beams has a sinusoidal intensity distribution and the pattern is shifted within the imaging plane in a direction perpendicular to the interference pattern in accordance with the phase shift error of the phase shifters. Thus, by detecting the amount of positional shift of the interference pattern (the phase shift of the sinusoidal wave), it is possible to determine the error in the amount of phase shift. In this case, in order to enhance the contrast of the interference pattern, it is preferable to select the ratio between the areas of the phase-shifter deposited portions and the phase-shifter non-deposited portions to be in the range from 7:1 to 7:2 or 1:7 to 2:7. In accordance with the construction which obtains the amount of phase shift from the amount of positional shift of the interference pattern, the S/N ratio is improved and the measurement with a high degree of accuracy is realized as compared with the case in which the amount of phase shift is determined through the light intensity detection.

In accordance with a third aspect of the present invention, there is provided an inspection apparatus comprising: an illumination optical system for illuminating a pattern on a mask to be inspected; an imaging optical system for focusing at a given imaging position an image of the pattern to be inspected produced by an illuminating light beam from the illumination optical system; light beam deflecting means for changing the direction of incidence of the illuminating light beam to the mask in such a manner that the illuminating light beam falls on the mask at a given angle of incidence and that of the light beams transmitted through the pattern to be inspected the 0-order diffracted beam and either one of the ±first-order diffracted beams are passed substantially through the Fourier transform plane within the imaging optical system substantially symmetrically with respect to the optical axis of the imaging optical system; and pattern detecting means arranged at or near the imaging position to photoelectrically detect the image of the pattern to be inspected focused by the imaging optical system.

The inspection apparatus according to the third aspect is constructed so that the illuminance distribution at substantially the Fourier transform plane (the pupil plane or its conjugate plane within the illumination optical system is adjusted in such a manner that only that light beam obliquely incident on the mask from a given direction and at a given angle is used as the illuminating light and a pattern image (interference pattern) by the two light beams including the 0-order diffracted beam and either one of the ±first-order diffracted beams is formed, thereby determining the error in the amount of phase shift from the amount of positional shift of the interference pattern (the phase shift of the sinusoidal wave). Therefore, as in the case of the inspection apparatus according to the second aspect, an excellent S/N ratio is obtained and also a highly accurate measurement is realized. Also, this inspection apparatus is constructed so that the two light beams (the 0-order diffracted beam and either one of the ±first-order diffracted beams) concerning with the image forming are passed through optical paths which are symmetrical with respect to the optical axis, with the result the position of the interference pattern is not changed due to a wave front aberration, spherical aberration or the like caused by the deviation (defocusing) of the detecting means from the imaging plane and a highly accurate measurement is possible.

The above and other features and advantages of the present invention will be understood more clearly from the following description of its preferred embodiments taken in conjunction with the accompanying drawings.

BRIEF DESCRIPTION OF THE DRAWINGS

FIGS. 7a to 7c, 8a to 8c and 9a to 9c show examples of light quantity distributions obtained by the inspection according to the first embodiment of the present invention.

FIGS. 24 and 25 show the constructions of modifications of the inspection apparatus according to the fifth embodiment of the present invention.

DESCRIPTIONS OF THE PREFERRED EMBODIMENTS

Embodiment 1

Figure 1:
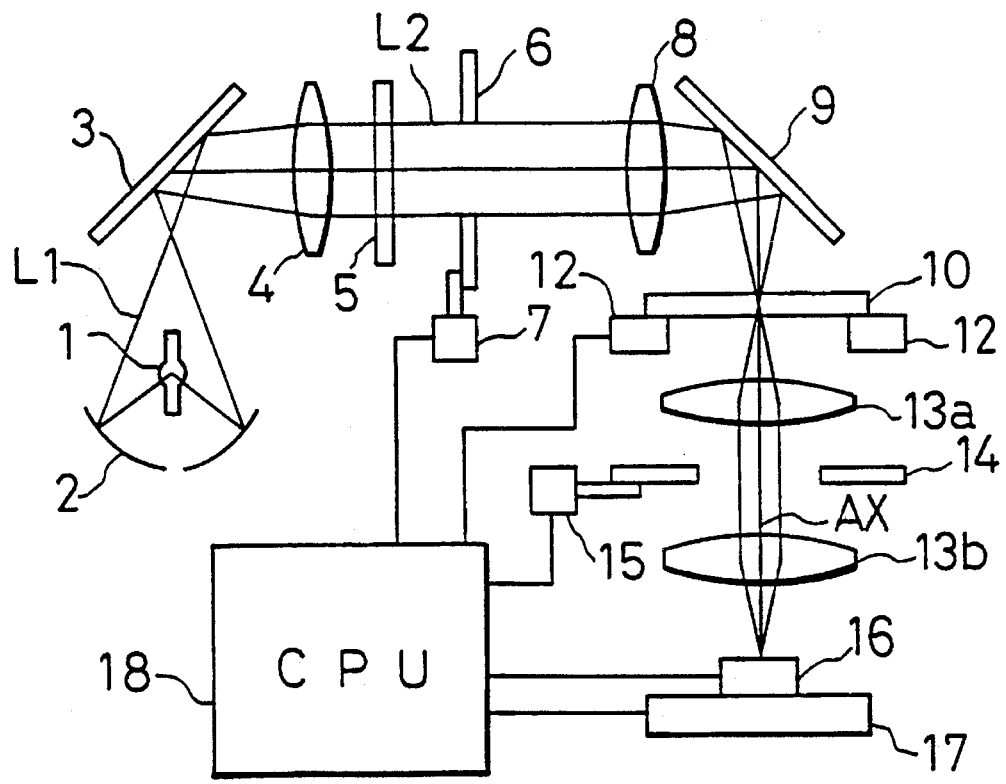
FIG. 1 is a schematic diagram showing the construction of a phase-shifted reticle inspection apparatus according to a first embodiment of the present invention.

FIG. 1 shows a schematic construction of a phase-shifted reticle inspection apparatus according to a first embodiment of the present invention. The light beam L1 from a light source 1 is projected onto an interference filter 5 through an ellipsoidal mirror 2, a reflecting mirror 3 and an optical system 4. A light beam L2 selected by the interference filter 5 and having a wavelength substantially equal to the exposure light wavelength is projected onto a reticle 10 through a variable aperture stop 6, an optical system 8 and a mirror 9 by the critical illumination method. Note that an illumination optical system is formed by the component parts including from the light source 1 to the mirror 9 in the order of these reference numerals, and the variable aperture stop 6 is arranged at the Fourier transform plane, the pupil conjugate plane or near thereat within the illumination optical system for the pattern surface of the reticle 10. The light beam transmitted through the reticle 10 is condensed on a detector 16 through an inspection optical system including optical systems 13a and 13b and a variable aperture stop 14. The variable aperture stops 6 and 14 are arranged so as to be conjugate with each other and in this embodiment the variable aperture stop 14 is arranged at the Fourier transform plane within the optical systems 13a and 13b. The information detected by the detector 16 and relating to the light quantity distribution is applied to a processing circuit 18. The processing circuit 18 computes a light quantity ratio in accordance with the applied information relating to the light quantity distribution. Note that the openings of the variable aperture stop 6 and the variable aperture stop 14 in the inspection optical system are respectively varied by motors 7 and 15. Also, the reticle 10 and the detector 16 are respectively held and are movable at least in the direction of the optical axis AX by drivers 12 and 17.

At this time, the transmitted beam and the diffracted beam are generated from the reticle 10 illuminated by the light beam L2 so that these beams are condensed near to the detector 16 through the inspection optical systems 13a and 13b and a projection image of the reticle 10 is focused. The detector 16 comprises a two-dimensional image sensor or one-dimensional sensor such as an image pickup tube or image pickup device and it detects the light quantity distribution in a part of the projection image of the reticle 10. It is to be noted that if the movable member 17 is also movable within the plane perpendicular to the optical axis AX of the inspection optical system, the detector 16 may be composed of a combination of a single slit or a plurality of slits and a photomultiplier or photodiode. In this case, while moving the movable member 17 within the plane perpendicular to the optical axis AX, the light quantity is detected and the light quantity distribution of the reticle pattern image is detected. The detected light quantity distribution is processed by the processing ciucuit 18 and the light quantity at each of the various parts in the projection image of the line and space pattern. If necessary, the light quantity distribution may be stored in the processing circuit 18.

While, in this embodiment, the illumination method is the critical illumination method, the same effect may be obtained by the use of the Köhler's illumination system. Also, the light source is a bright-line lamp such as a mercury-vapor lamp or a laser.

Figure 2:
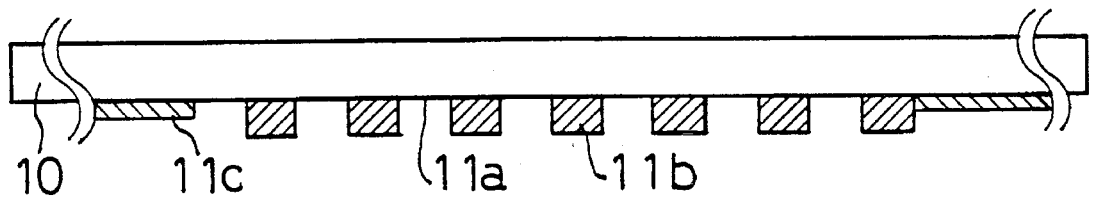
FIGS. 2 and 3 are sectional views respectively showing the configurations of patterns on the phase-shifted reticles used with the first embodiment of the present invention.

FIG. 2 is a sectional view showing the configuration of the pattern on the phase-shifted reticle used in this embodiment of the present invention. Phase-shifter deposited portions 11 and non-deposited portions 11a are alternately arranged at substantially the same ratio of 1:1 and equal in number with each other and these portions are in the form of uniform lines each extending in the perpendicular direction to the paper plane of the Figure. Chromium films 11c block the light to the areas other than the deposited portions 11b and the non-deposited portions 11a. Note that while, in the present invention, the deposited portions 11b and the non-deposited portions are equal in number, i.e., 7, there is no need to limit them in number.

Figure 3:
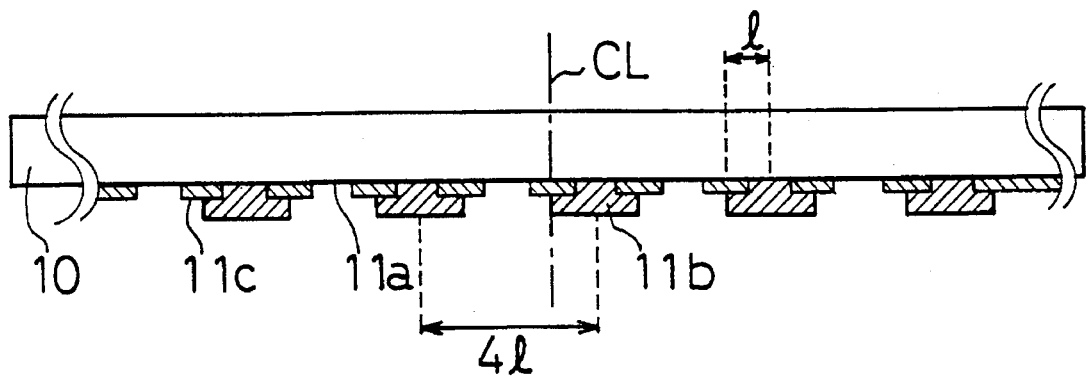

FIG. 3 is a sectional view showing the configuration of the pattern on another example of the phase-shifted reticle used with this embodiment of the present invention. The chromium films 11c are deposited in the form of a line and space pattern at substantially the 1:1 ratio (the duty ratio is 1:1), and the phase shifter is formed at each alternate opening of the chromium films 1c. The arrangement of the phase-shifter deposited portions 11b and the non-deposited portions 11a is the same as in the case of FIG. 2.

Next, the method of determining the error in the amount of phase shift according to the present embodiment of the invention will be described; in accordance with the present embodiment the amount of error in the phase difference due to the phase shifters can be measured in all the same way even if either of the reticles of FIGS. 2 and 3 is used and therefore the method will be explained by taking the case in which the pattern of FIG. 3 is used.

Firstly, it is assumed that the reticle of FIG. 3 has the line and space pattern in which the pitch of the chromium films 11c is 2 1. In this case, the pitch of the deposited portions 11b becomes 4 1 so that the ±first-order diffracted beams generated from the deposited portions of the reticle 10 are generated in the directions having the angles of ±θ (rad) with respect to the incident light and the transmitted beam (0-order beam) passed through the non-deposited portion 11a. This θ represents the angle given by the following $$\sin\theta = \lambda/4\ 1$$

[λ=incident light (illuminating light) wavelength]

Where the phase-shifted reticle having the line and space pattern 11a to 11c with the pitch of 2 1 as in the case of FIG. 3 is to be inspected, the aperture stop 14 is set in such a manner that the numerical aperture NA of the inspection optical system 13a, 13b becomes about NA=1.5×sin θ thereby preventing the diffracted beams of the higher orders than the second order from falling on the inspection optical system 13a, 13b. Also, in order that the numerical aperture NA of the optical system 4 and the optical system 8 may become about NA=0.3×1.5×sinθ, the aperture stop 6 is set so as to enhance the coherence of the illuminating light on the line and space pattern 11a to 11c. In other words, while, in this case, the coherence factor σ of the illumination system (illumination system numerical aperture/imaging system numerical aperture) is 0.3, the value of σ should preferably be selected to be in the range from 0.1 to 0.3. In this condition, the reticle 10 or the detector 16 is set to a given position (defocus position) in the direction of the optical axis AX of the inspection optical system 13a, 13b by the driver 12 or 17 and the light quantity distribution is detected by the detector 16. At this time, each of the drivers 12 and 17 should preferably be provided with position measuring means such as a linear encoder or laser interferometer so as to confirm the position of the reticle 10 and the detector 16. The light quantity distribution obtained by illuminating the reticle 10 by the illuminating light L2 from the light source 1 and then receiving the light quantity of the projection image of the reticle 10 is transferred as an electric signal to the processing circuit 18. In the processing circuit 18, of the light quantity distribution signal the light quantity of the image of the deposited portions 11b of the reticle 10 and the light quantity of the image of the non-deposited portions 11a are respectively measured and the ratio between these light quantities is determined. In accordance with the thus determined light quantity ratio, the pattern size of the measured pattern (in this case the width l of the chromium films 11c) and the set positions of the reticle 10 and the detector 10 in the direction of the optical axis AX, the error in the amount of phase shift due to the phase shifters 11b is obtained.

More specifically, assuming here that the reticle 10 is fixed in place, that l represents the width of the chromium films 11c having the pitch of 2 1, ΔF the set position of the detector 16 which is shifted from the best imaging plane (with the imaging position as 0, the direction tending toward the detecting optical system is assumed as minus or '−'), λ the wavelength of the illuminating light, and that the amount of phase shift of the phase shifters 11b is based on the design value π (rad) and its error is represented by δ (rad), then the intensity distribution of the projection image on the detector 16 is given by the following expression (1)

$$|\{1-\exp(i\delta)\}-\{1+\exp(i\delta)\}(4\sqrt{2}/\pi)\times\exp(-i\pi\Delta F\lambda/16\ l^2)\cdot\sin(2\pi x/4\ l)|^2 \quad (1)$$

here i represents the complex number, and also in FIG. 3 the center line CL passing through the boundary between the phase-shifter deposited portion 11b and the non-deposited portion 11a is represented as x=0 with the right side to it being assumed as plus or '+'.

Thus, by comparing the light quantity ratio computed from the resulting light quantity distribution and the ratio of the integrated value according to 0<x<2 1 of the intensity distribution indicating expression (1) to the integrated value according to −2 1<x<0, it is possible to determine the error δ (rad) in the amount of phase-shift due to the phase shifters 11b. In other words, this means that the design relation between the phase difference and the light quantity ratio obtained from the expression (1) and the light quantity ratio obtained as the result of the measurement are compared with each other to obtain the phase difference produced by the phase shifters 11b of the reticle 10 and the difference between this phase difference and the phase difference (π) of the design value is obtained.

Alternatively, the error δ can be obtained by determining the peak intensity of the image of the deposited portions 11b and the peak intensity of the image of the non-deposited portions 11a and then comparing the ratio between these intensities and the ratio between the values obtained by respectively substituting x=+1 and x=−1 into the expression (1) in the precessing circuit 18.

It is to be noted that in order to improve the measurement accuracy, it is possible to move the position of the detector 16 or the reticle 10 to another position in the direction of the optical axis AX of the inspection optical system 13a, 13b so as to make the measurement again and thereby to average the results of the plurality of measurements.

Then, where the phase shifters 11b absorb the light or the line/space ratio of the chromium films 11c is not 1:1, there is no error in the phase difference and also it is expected that the light quantity ratio between the images of the deposited portions 11b and the non-deposited portions 11a fails to become 1:1 even if the measurement is made at the imaging position. In this case, it is necessary to measure the transmittance of each portion of the deposited portions 11b and the non-deposited portions 11a and thereby to provide a suitable compensation for the above-mentioned light quantity ratio. Where the phase shifters 11b do not absorb the light, the line/space ratio of the chromium films 11c is 1:1 and there is no error in the phase difference, when the detection is effected at the imaging position, the light quantity ratio of the resulting images becomes 1:1 as will be described later.

Then, a description will be made of the measurement of the transmittance at each portion of the deposited portions 11b and the non-deposited portions 11a. This is effected in a manner that the aperture stop 14 is set so that the numerical aperture NA of the inspection optical system becomes greater than about 3.0×sinθ (sinθ=λ/4 1) and also the aperture stop 6 is similarly set so that the numerical aperture NA of the optical systems 4 and 8 becomes greater than about 3.0×sinθ and that the illumination is effected such that the coherence factor σ becomes substantially 1. At this time, the coherence of the illuminating light at the reticle 10 is deteriorated very greatly so that the transmitted beam from the deposited portion 11b and the transmitted beam from the adjacent non-deposited portion 11a do not practically interfer with each other. As a result, the line and space pattern which is proportional only to the transmittances is projected onto the detector 16 and the simple transmittances of the respective deposited portions 11b and non-deposited portions 11a can be measured. The results are fed back to the measurement results in the previously mentioned high coherence condition of the illuminating light. This may for example be effected by such processing as dividing the resulting light quantity distribution by the transmittances of the respective patterns.

Next, the transmittance compensation processing based on each light quantity distribution obtained by the detector 16 will be described with reference to FIGS. 4, 5 and 6.

Figure 4:
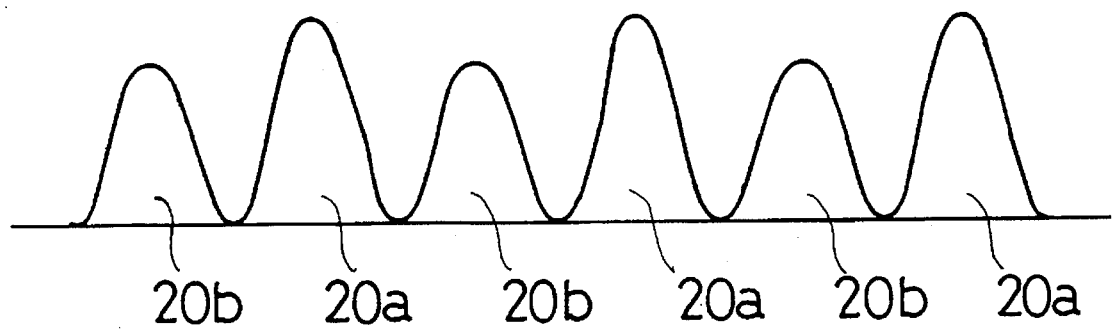
FIG. 4 shows the light quantity distribution in a condition where the illuminating light is high in coherence, the numerical aperture NA of the inspecting optical system is on the order of 1.5×sinθ, and the detector is shifted (defocused) from the imaging position.

FIG. 4 is a diagram showing the light quantity distribution in the condition where the illuminating light is high in coherence, the numerical aperture NA of the inspection optical system 13a, 13b is about 1.5×sinθ and the detector 16 is shifted (defocused) from the imaging position. Similarly, FIG. 5 is a diagram showing the light quantity distribution in the condition where the illuminating light is low in coherence, the numerical aperture NA of the inspection optical system 13a, 13b is about 3.0×sinθ and the detector 16 is at the imaging position (focus position). In the Figures, waveform portions 20a and 21a indicate the light quantities at the positions corresponding to the non-deposited portions 11a and waveform portions 20b and 21b indicate the light quantities at the positions corresponding to the deposited portions 11b.

Figure 5:
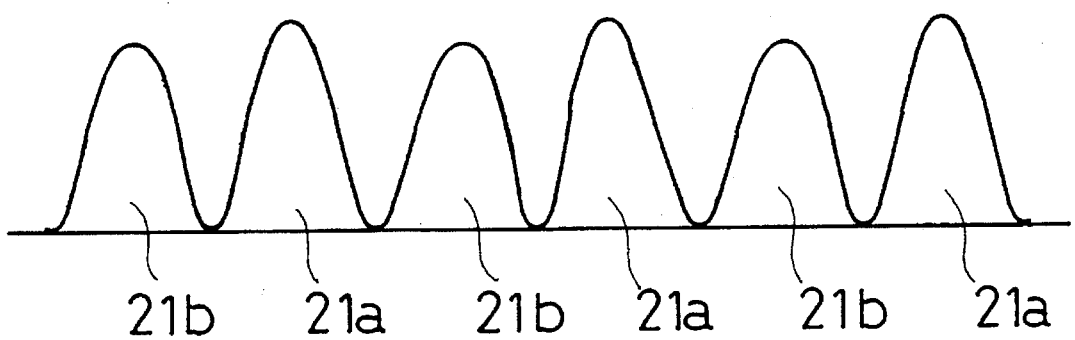
FIG. 5 is a diagram showing the light quantity distribution in a case where the illuminating light is low in coherence, the numerical aperture NA of the inspecting optical system is on the order of 3.0×sinθ, and the detector is at the imaging position (focuse position)

In FIG. 5 the difference between the waveform portions 21a and 21b indicates only the difference in transmittance, and in FIG. 4 the difference between the waveform portions 20a and 20b involves the difference in transmittance and the error in the phase difference. As a result, it is possible to determine the value of the waveform portion 21a: the waveform portion 21b (the ratio between their integrated values or the ratio between their peak values may also be used) so that the resulting value is used to divide the light quantity distribution, the integrated value or the peak values of the waveform portions 20b and thereby to compensate the transmittance.

Figure 6:
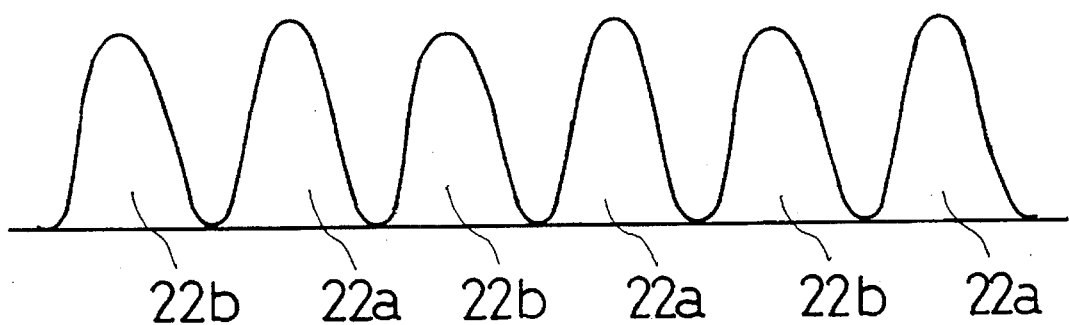
FIG. 6 shows the light quantity distribution resulting from the compensation of the transmittance.

FIG. 6 is a diagram showing the light quantity distribution resulting from the compensation of the transmittance. By determining the light quantity ratio between the waveform portions 22a and 22b in accordance with the illustrated distribution and comparing it with the expression (1), it is possible to measure the amount of phase shift without being subjected to the effect of the light absorption by the phase shifters and the effect of the patterning error of the chromium films 11c (i.e., the effect of the fact that the line/space ratio is not 1:1). It is to be noted that while, in cases where the coherence of the illuminating light is high, the transmittance of the pattern can be measured if the detector is at the imaging position (the best focus position), the measurement is subject to the effect of the adjacent pattern and therefore it is impossible to expect a satisfactory accuracy.

In this connection, the detection and calibration of the imaging position can be effected by increasing the coherency of the illuminating light, moving the detector 16 or the reticle 10 in the direction of the optical axis AX, detecting the amount of transmitted light of the phase-shifted line and space pattern whose phase difference is intentionally deviated from 180° and selecting as the imaging position that point where the light quantity ratio between the phase-shifter deposited portions 11b and non-deposited portions 11a becomes 1:1 after the transmittance compensation. Alternatively, it is possible to select as the imaging position that point where the contrast of the phase-shifted line and space pattern becomes maximum in the condition where the coherence of the illuminating light is low and the numerical aperture of the inspection optical system 13a, 13b is on the order of 3.0×sinθ.

In accordance with the present invention, while the magnification of the inspection optical system 13a, 13b may be selected as desired, the measurement of the light quantity distribution is easy if the pattern 11a to 11c on the reticle 10 is magnified over the detector 16. In this case, instead of moving the reticle 10 in the direction of the optical axis AX of the inspection optical system 13a, 13b, the detector 16 may be advantageously moved since the accuracy of position setting becomes less severe by an amount corresponding to the square of the magnification.

On the other hand, where the detector 16 is combined with a photomultiplier with multiple slits in a line and space form or photodiodes, if the spacing of the multiple slits is selected 4 1 in terms of the magnification on the reticle surface side, the light quantity distributions of a plurality of phase-shifter patterns (the deposited portions 11b) and a plurality of reticle bare surface patterns (the non-deposited portions 11a) can be detected simultaneously and a reduction in the detection time can be attained.

Figure 8A:
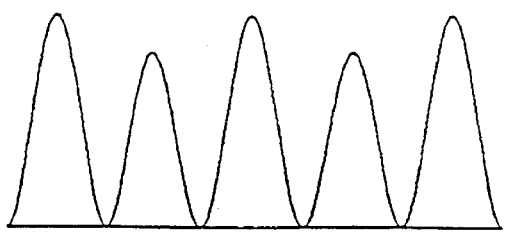
Figure 9A:
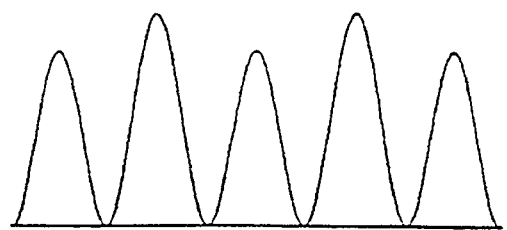
Figure 8B:
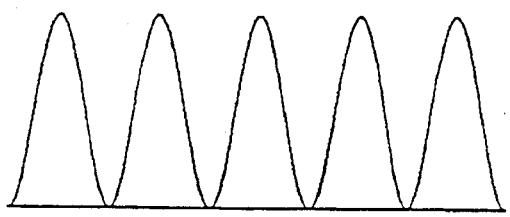
Figure 9B:
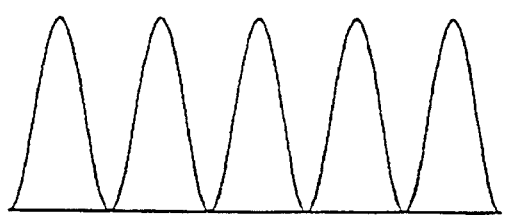
Figure 8C:
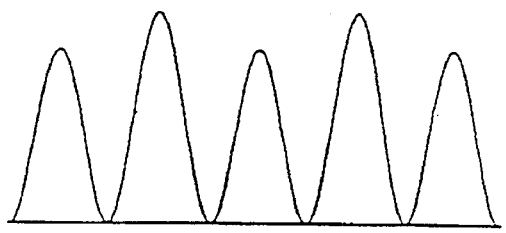
Figure 9C:
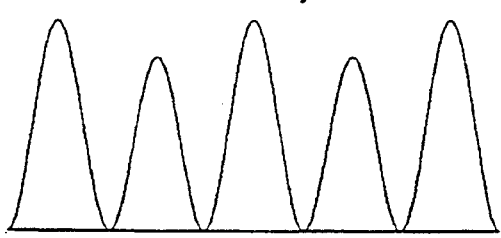

FIGS. 7a to 7c, 8a to 8c and 9a to 9c are diagrams showing examples of the light quantity distribution obtained by performing the inspection method according to the embodiment of the present invention. In this case, the width l of the chromium film patterns is 2 μm in all the Figures and the wavelength of the illuminating light is the i line (0.365 μm) of Hg bright line. FIGS. 7a to 7c show the case in which the phase difference produced by the phase shifters is exactly 180°, FIGS. 8a to 8c similarly show the case of 170° and FIGS. 9a to 9c similarly show the case of 190°. FIGS. 7a, 8a and 9a show the light quantity distribution waveforms obtained when the detector 16 is at a position which is deviated from the imaging position of the reticle 10 through the inspection optical system (apart from the inspection optical system) by +75 μm, for example. Similarly, FIGS. 7b, 8b and 9b show the light quantity distribution waveforms obtained when the detector 16 and the reticle 10 are accurately in the imaging relation. Also, FIGS. 7c, 8c and 9c show the light quantity distribution waveforms obtained when the detector 16 is deviated by for example −75 μm (moved toward the inspection optical system). While the number of the peaks shown in each of the Figures is 5, the number of peaks which can be obtained by the detection is not limited to 5. Note that in each of the Figures the three waveforms at the center and the ends correspond to the non-deposited portions 11a and the remaining two waveforms correspond to the deposited portions 11b.

The amounts of deviation (ΔF) of the position of the detector 16 from the imaging position, i.e., +75 μm, 0 μm and −75 μm respectively correspond to +75/$\beta^2$ μm, 0 μm and −75/$\beta^2$ μm when reduced to the amounts of deviation on the detector 16 side in terms of the magnification with β representing the magnification of the inspection optical system. In other words, it is equivalent as a matter of principle even if the detector 16 is fixed in place and the reticle 10 is deviated by +75/$\beta^2$ μm, 0 μm and −75/$\beta^2$ μm, respectively, and all the same results as FIGS. 7a to 7c, FIGS. 8a to 8c and FIGS. 9a to 9c are obtained. Note that the imaging position 0 and the direction tending toward the inspection optical system is represented as '−'.

The reason why the difference in light quantity between the images of the deposited portions and the non-deposited portions is caused at a defocus position will now be described.

The amplitudes of the diffracted beams generated from the phase-shifted reticle pattern shown in FIG. 3 are as follows, $$\text{0-order beam: } 1 - e^{i\delta} \quad (2)$$

$$\text{+first-order beam: } \frac{2\sqrt{2}}{\pi} (1 + e^{i\delta})$$

$$\text{−first-order beam: } \frac{2\sqrt{2}}{\pi} (1 + e^{i\delta})$$

Also, as regards their directions, the 0-order beam is in the optical axis direction, the +first-order beam is in the direction inclined from the optical axis by +θ and the −first-order beam is in the direction inclined from the optical axis by θ. When these three beams are condensed by the inspection optical system so that they reach the detector, the directions of travel of the +first-order beam and the −first-order beam are changed with each other.

At this time, if the detector is not at the accurate image position of the phase-shifted reticle pattern or it is in a defocused condition, the ±first-order beams passing through the locations apart from the optical axis produce phase differences (the wave front aberrations due to the defocusing) with respect to the 0-order beam passing by near the optical axis within the detection optical system.

If ΔF represents the amount of defocusing, this phase difference is given by $-\pi\Delta F\lambda/16\ l^2$ [rad]. Therefore, in accordance with the following 0-order beam: $1-\exp(i\delta)$ first-order beam: $\exp(-i\pi\Delta F\lambda/16\ l^2)$ (2 $\sqrt{2}/\pi$)·{$1+\exp(i\delta)$}·$\exp(-2i\pi x/4\ l)$ −first-order beam: $\exp(-i\pi\Delta F\lambda/16\ l^2)$ (2 $\sqrt{2}/\pi$)·{$1+\exp(i\delta)$}·$\exp(+2i\pi x/4\ l)$ the sum of the amplitude distributions of the three beams on the detector is given by $$\{1 - \exp(i\delta)\} + (4\sqrt{2}/\pi) \cdot \{1 + \exp(i\delta)\} \cdot \quad (3)$$

$$\cos(2\pi\ x/4l) \cdot \times \exp(-i\pi\ \Delta\ F\ \lambda/16l^2)$$

Note that the intensity is the square of the absolute value of the expression (3). Also, since the boundary CL between the phase shifter film deposited pattern and the non-deposited pattern is given as x=0 in the expression (1), the term sine is used in place of the cosine in the expression (3).

On the other hand, instead of multiplying the position item by $\exp(-i\pi\Delta F\lambda/16\ l^2)$ as the phase shift of the first-order beam with respect to the 0-order beam, the 0-order beam may be multiplied by $\exp(+i\pi\Delta F\lambda/16\ l^2)$.

Therefore, in place of the expression (3), the sum of the amplitude distributions is given by $$\{1 - \exp(i\delta)\} \cdot \exp(i\pi\ \Delta\ F\ \lambda/16l^2) + (4\sqrt{2}/\pi) \cdot \{1 + \exp(i\delta)\}(2\pi x/4l) \quad (4)$$

Then, where the value of δ is small, that is, where the amount of phase shift of the shifters is substantially π, we may state as follows $$\{1-\exp(i\delta)\} = 1-\cos\delta - i\sin\delta \approx -i\cdot\sin\delta$$

$$\{1+\exp(i\delta)\} = 1+\cos\delta + i\sin\delta \approx 2$$

therefore, the expression (4) becomes as follows $$-1 \cdot \sin\delta \times \exp(\pi\ i\ \Delta\ F\ \lambda/16l^2) = \quad (5)$$

$$-\sin\delta \times \sin(\pi\ \Delta\ F\ \lambda/16l^2) - \sin\delta \times$$

$$\cos(\pi\ \Delta\ F\ \lambda/16l^2) + (8\sqrt{2}/\pi) \cdot \cos(2\pi\ x/4l)$$

While the intensity is the square of the absolute value of the expression (5), the imaginary part of the expression (5) does not include x and thus there is no position dependency. Therefore, the intensity is constant with respect to the position.

The fact that the pattern of the phase-shifter deposited portions and the pattern of the non-deposited portions are different in intensity can be explained by considering only the real part of the expression (5).

The real part of the expression (5) or the following is the cosin function plus the offset term (not dependent on the position x) which is determined by δ and ΔF. If the value of sinδ is not 0 (that is, there is no error in the amount of shift), this offset term is proportional to $\sin(\pi\Delta F\lambda/16\ l^2)$. Also, since $\sin(\pi\Delta F\lambda/16\ l^2) \approx \pi\Delta F\lambda/16\ l^2$ if the value of ΔF is small, the offset term is approximately proportional to the amount of defocus ΔF.

Figure 10A:
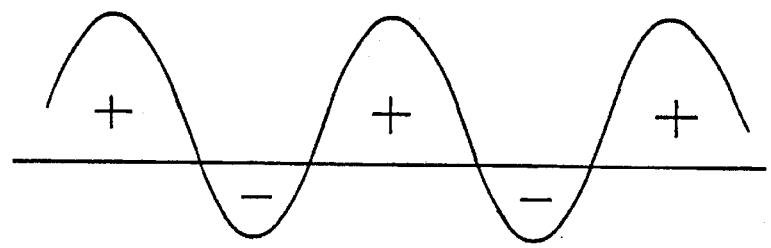
FIGS. 10a to 10f are diagrams for explaining the principles by which variation in the light quantity of an image is caused by the defocusing.
Figure 10B:
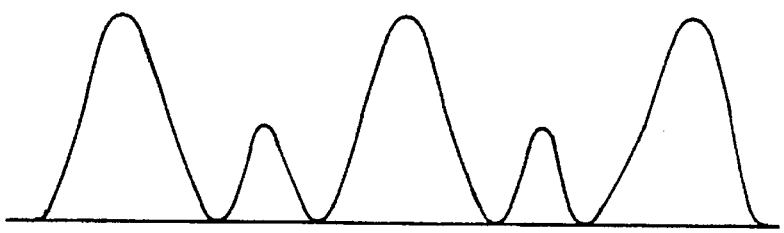

FIGS. 10a to 10f are graphs each showing the real part of the expression (5) or its square. FIG. 10a shows the real part when the offset is positive. The fact that the offset is positive means that $\sin(\pi\Delta F\lambda/16\ l^2)$ is negative when sin δ>0 and that ΔF<0 when the value of ΔF is very small. FIG. 10b shows the square of this amplitude (of the real part) and it represents the light intensities. While, in the actual image, the square of the imaginary part of the expression (5) is added as the offset to it, the alternate peaks or the pattern portion of the phase-shifter deposited portion and the pattern portion of the non-deposited are apparently different in light quantity with each other.

Figure 10C:
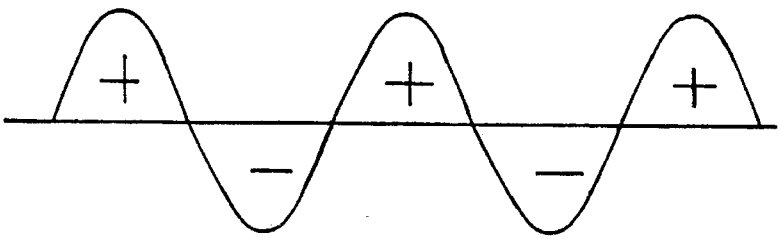
Figure 10D:

On the other hand, FIG. 10c and 10d show the cases where the offset is 0, that is, sin δ=0 or $\sin(\pi\Delta F\lambda/16\ l^2)=0$ and the light quantities of all the patterns are equal.

Figure 10E:
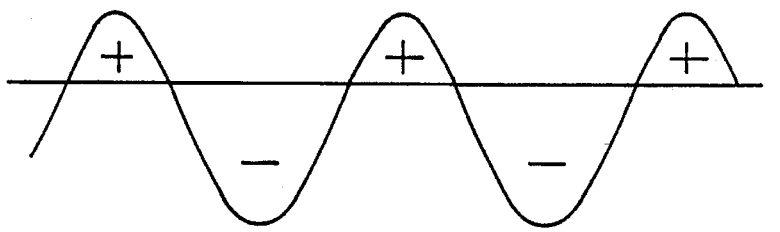
Figure 10F:
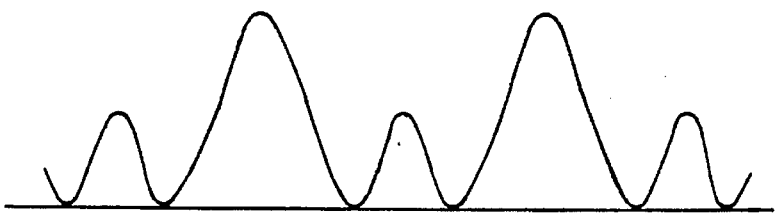

FIGS. 10e and 10f show the case where the offset is negative, that is, if δ>0, for example, $\sin(\pi\Delta F\lambda/16\ l^2)$ is positive or ΔF>0. In this case, the intensities of the peaks in FIG. 10f are in reverse relation with those in the case of FIG. 10b.

From the foregoing principle it will be seen that when there is an error in the amount of phase shift and the light quantity detection is effected at a defocus position, the resulting two pattern images differ in light quantity from each other.

Figure 11:
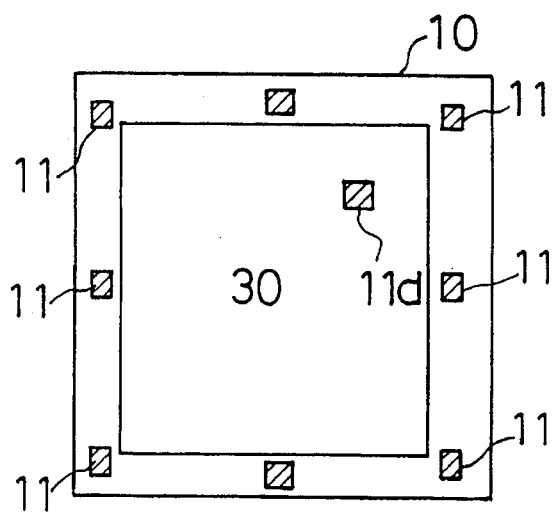
FIG. 11 shows an exemplary configuration of the inspection phase shifter pattern on the reticle used for the inspection according to the first embodiment of the present invention.

FIG. 11 shows an example of the configuration of the reticle inspection phase shift pattern used for the inspection according to the embodiment of the present invention. Phase shift patterns 11 for exclusive inspection purposes are arranged on the marginal area of a semiconductor circuit pattern 30. It is suffice if there is at least one of the phase shift patterns. Also, if there is a suitable pattern 11d within the semiconductor circuit pattern 30, no problem will be caused even if the inspection is effected by making use of this pattern. The exclusive inspection phase shift patterns 11 may be used as reticle alignment marks and it is also possible to transfer them onto a wafer for use as wafer alignment marks.

Figure 12:
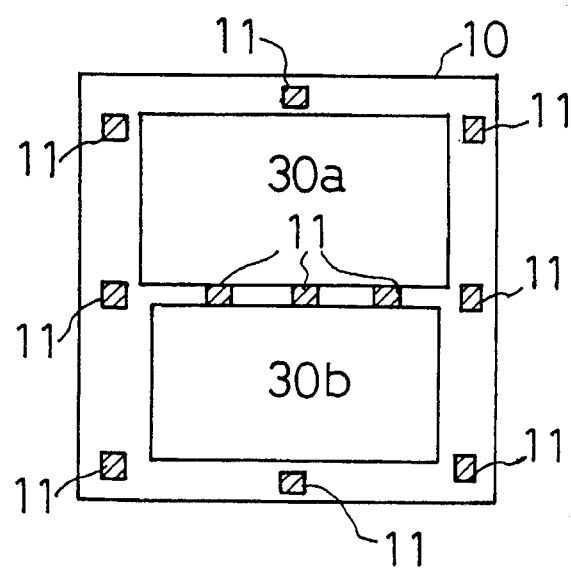
FIG. 12 shows another exemplary configuration of the inspection phase shifter pattern on the reticle used for the inspection according to the first embodiment of the present invention.

FIG. 12 shows another example of the arrangement of reticle inspection phase shift patterns used for the inspection according to the embodiment of the present invention. There are two semi-conductor circuit patterns 30a and 30b within a single reticle and in this case exclusive inspection phase shift patterns 11 may be provided within the street area between the circuit patterns 30a and 30b. These patterns 11 may also be used as alignment marks as in the case of FIGS. 7a to 7c.

In order to detect a plurality of inspection phase shift patterns arranged at given positions within a single reticle as in the case of FIGS. 11 and 12 by a single inspection optical system, it is only necessary to design so that the movable portion 12 for moving the reticle 10 is movable within substantially the size of the reticle 10 in the plane perpendicular to the optical axis of the inspection optical system or the plane parallel to the reticle 10.

Note that in accordance with the present embodiment, even if the phase-shifter deposited portions 11b and the non-deposited portions 11a are not equal in number, the phase-shift line and space pattern used for the inspection presents no particular problem if the coherence factor σ of the illuminating light has a relatively large value. In order to make the inspection accuracy best, however, it is desirable that the deposited portions 11b and the non-deposited portions 11a are equal in number.

Embodiment 2

Figure 13:
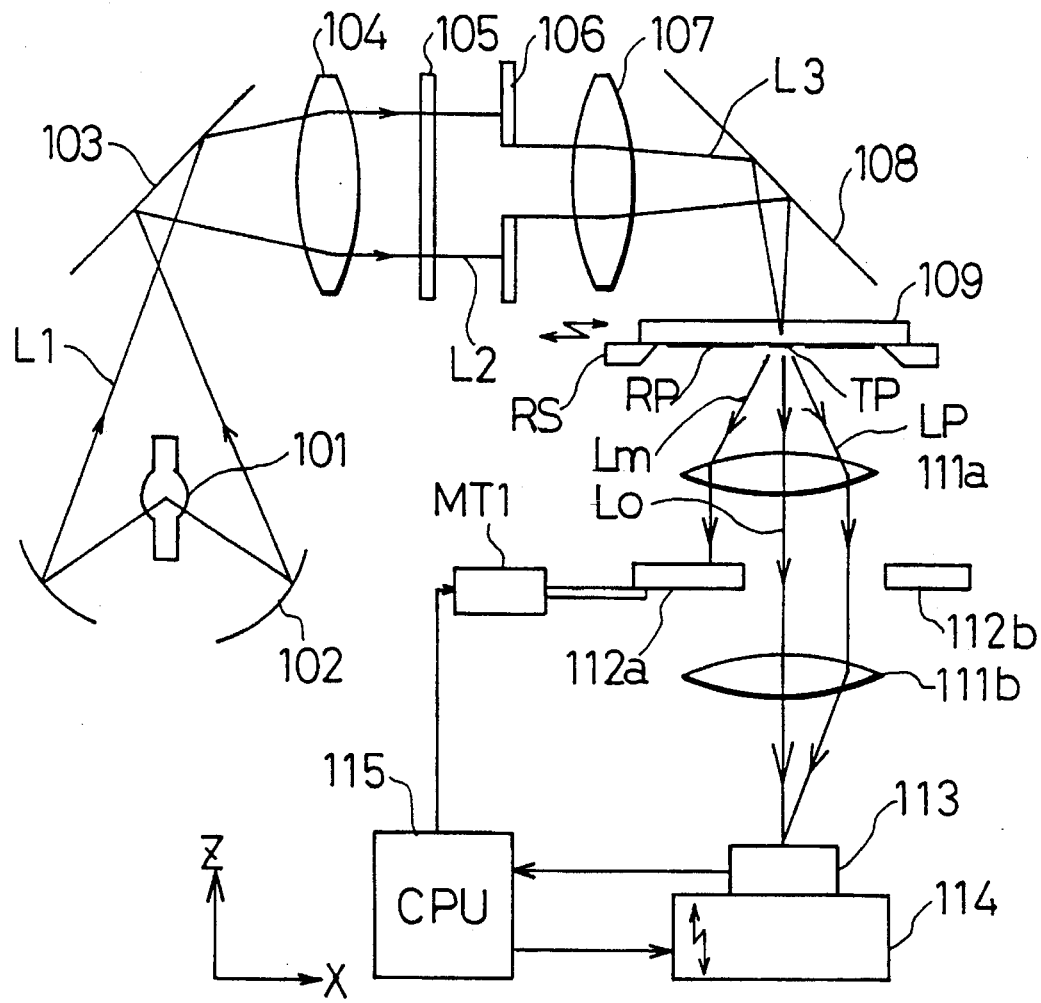
FIG. 13 is a schematic diagram showing the construction of an inspection apparatus according to a second embodiment of the present invention.

FIG. 13 is a schematic diagram showing the construction of a phase-shifted reticle inspecting apparatus according to a second embodiment of the present invention. In the Figure, the light emitted from a mercury vapor lamp 101 forming a light source is condensed (L1 in the Figure) by an elliptical mirror 102 and bent by a mirror 103 to reach a relay lens 104. The light passed through the relay lens 104 is then monochromatized by a wavelength selecting element 105 such as an interference filter thus producing a monochromatic light (L2 in the Figure) of the same wavelength as the exposure light of an exposure apparatus in which a reticle 109 is to be used. This monochromatic light L2 is passed through an aperture stop 106, condensed (L3 in the Figure) by a condenser lens 107 and directed by a mirror 108 to reach the reticle 109 to be inspected.

In this case, at least one of the elliptical mirror 102 and the mirror 103 may be comprised of a dichroic mirror and in this case the wavelength selecting element 105 can be eliminated. Also, where a laser (e.g., KrF excimer laser or the like) is used as the light source of the exposure apparatus, the inspection apparatus may correspondingly use as its light source the laser in place of the mercury vapor lamp 101. Also, while the illumination system (101 to 108) of the above-mentioned apparatus is the critical illumination, it is of course possible to use the Köhler illumination.

Figure 18:
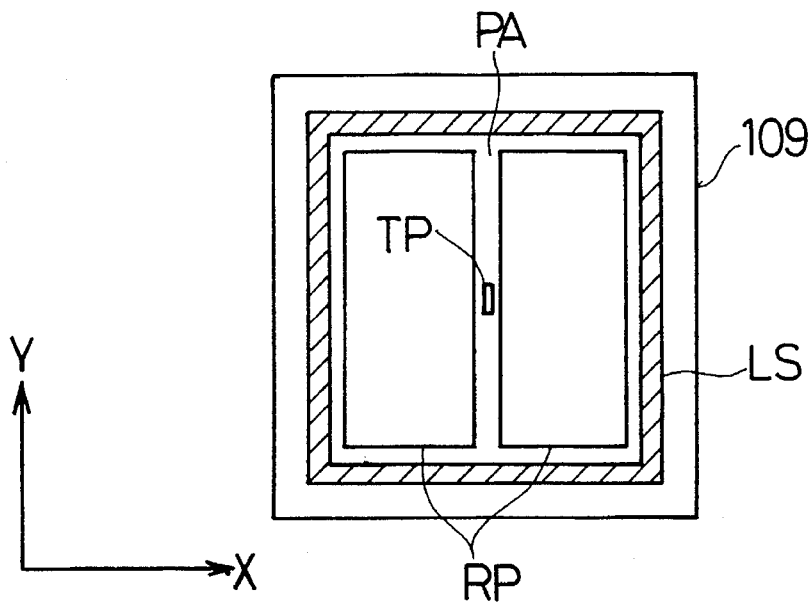
FIG. 18 shows an example of the reticle used with the apparatus according to the second embodiment of the present invention.

The reticle 109 is mounted on a stage RS which is two-dimensionally movable in a horizontal plane and circuit patterns PR (which will be described later) are formed on the lower surface of the reticle. FIG. 18 is a plan view showing an example of the reticle used in the apparatus according to the present embodiment. In FIG. 18, a pattern to be inspected is formed, along with the circuit patterns PR, within a pattern area PA (in this case, the region corresponding to the street line) surrounded by a light shielding material DS such as chromium. Thus, with the reticle 109 being held on it, the stage RS is driven by a motor which is not shown in a manner that the inspection pattern comes into the illumination area of the light beam L3. As a result, the illuminating light L3 illuminates the vicinity of the pattern to be inspected in the reticle 109.

The illuminating light L3 is diffracted by the pattern to be inspected thereby producing a 0-order diffracted beam $L_o$, a +first-order diffracted beam $L_p$ and a −first-order diffracted beam $L_m$. While these three diffracted beams are all projected to a detection optical system 111a, either one of the +first-order beam $L_p$ and the −first-order beam $L_m$ is intercepted by a light shielding member (spatial filter) 112a or 112b arranged near the Fourier transform plane within the detection optical system 111a, 111b. FIG. 13 shows the case in which the −first-order beam $L_m$ is intercepted. The light shielding members 112a and 112b are driven by a motor $MT_1$ in response to drive commands from a control circuit 115. Note that the diffracted beams of the second and higher orders are blocked by the light shielding members 112a and 112b. As a result, the two light beams including the 0-order beam $L_o$ and the +first-order beam $L_p$ are passed through the detecting optical system 111b and are focused on detecing means 113. An image pickup device of the CCD type or the like, a photodiode with multiple slits or the like is used as the focused image detecting means 113.

Figure 14:
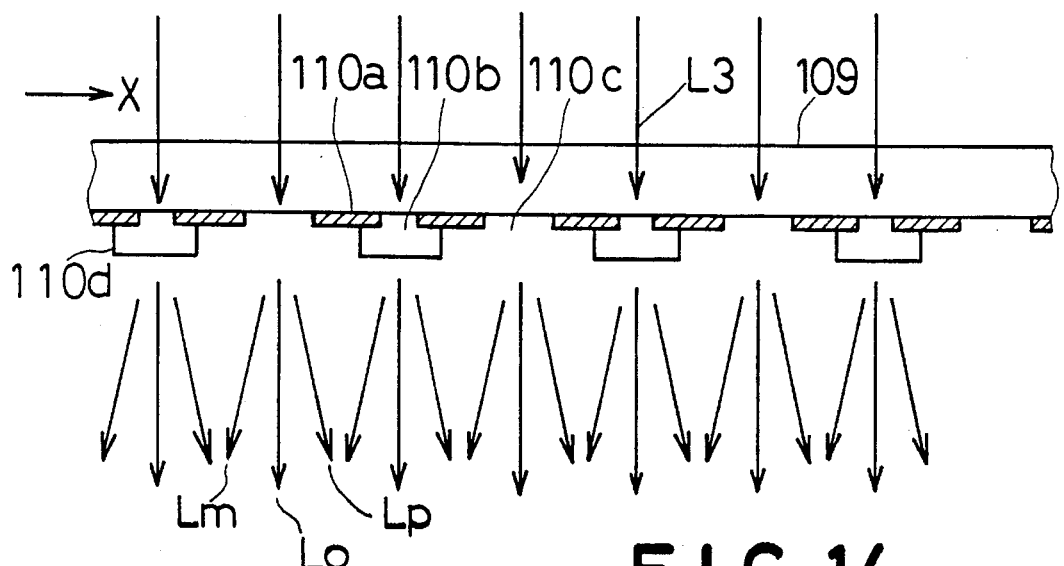
FIG. 14 is a schematic sectional view showing an example of the pattern to be inspected according to the second embodiment of the present invention.

The method of determining the error in the amount of phase shift according to the present embodiment will now be described. FIG. 14 is a schematic sectional view showing by way of example a pattern to be inspected according to the embodiment. Chromium films 110a are formed in a line and space configuration on the lower surface of the reticle substrate 109 and the widths of their openings (the space portions) are alternately reduced. A phase shifter 110d is deposited on each of the reduced openings. In other words, a pattern configuration is formed in which deposited portions 110b and non-deposited portions 110c of the phase shifters 110d are alternately arranged through the chromium films 110a.

The light beam L3 illuminating the reticle 109 from above is diffracted by the chromium films 110a, the deposited portions 110b and the non-deposited portions 110c thereby producing 0-order diffracted beams $L_o$, +first-order diffracted beams $L_p$ and −first-order diffracted beams $L_m$ as shown in FIG. 14.

At this time, the ratio among the amplitudes of the respective diffracted beams is such that if a represents the width of the non-deposited portions 110c, b the width of the deposited portions 110b, P the distance (pattern pitch) from the center of the non-deposited portion 110c to the center of the next non-deposited portion 110c, (π+δ) the phase change of the transmitted light due to the phase shifters 110d, 1 the amplitude transmittance of the non-deposited portions 110c, and t·exp(iδ) (0≤t≤1) the amplitude transmittance of the deposited portions 110b, then, on the basis of the center of the non-deposited portions 110c, the amplitude of the transmitted light is given by the following equation (6). In this connection, it is needless to say that this equation (6) corresponds to the expression (2) of the Embodiment 1 if a=b=1 and P=4 1.

$$D_0 = 1 - t \cdot e^{i\delta}$$

$$D_{\pm 1} = (P/\pi)\ [\sin(\pi a/P) + t \cdot \sin(\pi b/P) e^{i\delta}] \tag{6}$$

Figure 15A:
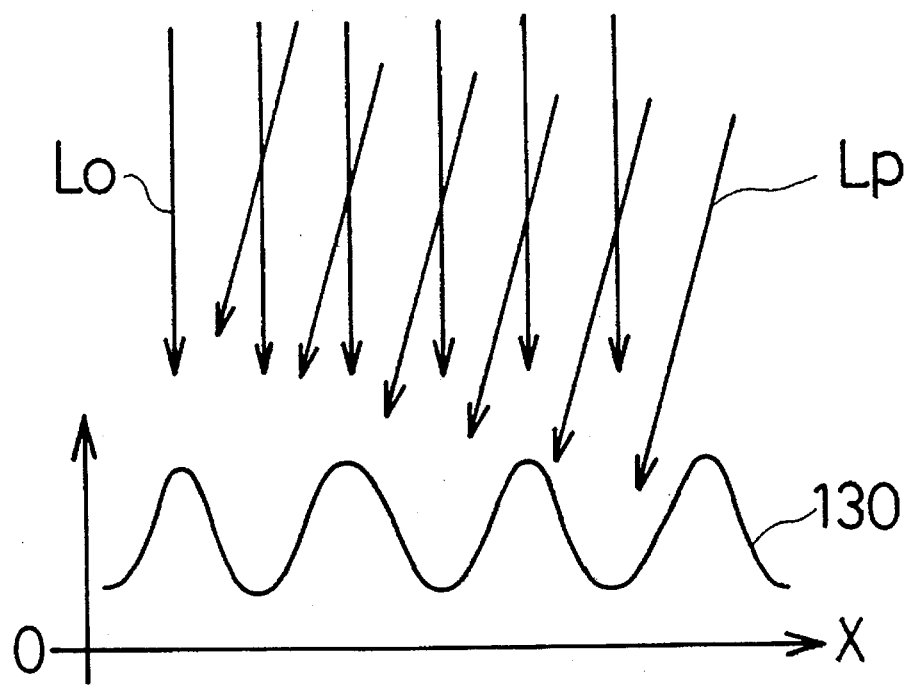
FIGS. 15A and 15B are diagrams for explaining the principle of the present invention.

At this time, the ±first-order beams proceed, in the plane of the paper in the Figure, in the directions of angles θ respectively given by ±sinθ=λ/P (λ is the wavelength of the illuminating light) with respect to the 0-order beam. With these three diffracted beams, if the −first-order beams are blocked and the 0-order beams and the +first-order beams are focused, an interference pattern 130 (shown as an amplitude distribution in the Figure) due to the interference of the two beams is produced as shown in FIG. 15A.

While the amplitudes of the 0-order beam and the +first order beam at the imaging position become as follows in the x direction (the direction of pattern arrangement), for example, $$D_0 = 1 - t \cdot e^{i\delta}$$

$$D_1 = (P/\pi)[\sin(\pi a/P) + e^{i\delta} \sin(\pi b/P)] \cdot e^{-2\pi ix/P} \quad (7)$$

if the beams are shifted from the imaging position and are defocused, its multiplication by a front wave aberration is performed. While the phases of the 0-order beam and the +first-order beam are important as the relative amounts, they are meaningless as the absolute amount and therefore the +first-order beam is multiplied by the phase difference between the +first-order beam and the 0-order beam or $e^{iw}$ as the front wave aberration.

As a result, the respective amplitudes are given as follows $$D_0 = 1 - t \cdot e^{i\delta}$$

$$D_1 = (P/\pi)[\sin(\pi a/P) + e^{i\delta} \sin(\pi b/P)] e^{-2\pi ix/(P+iw)} \quad (8)$$

At this time, the intensity distribution is the square of the absolute value of the sum of the amplitudes of the two beams so that if M represents the imaging magnification of the reticle pattern, we obtain the following $$P = a^2 + b^2 t^2 + 2abt \cdot \cos\delta + (P^2/\pi^2) [\sin^2(\pi a/P) + \quad (9)$$

$$t^2 \cdot \sin^2(\pi b/P) - 2t \cdot \sin(\pi a/P) \times \sin(\pi b/P) \cdot \cos\delta] +$$

$$(P/\pi) \cdot [\{a \cdot \sin(\pi a/P) - bt^2\sin(\pi b/P) - t \cdot [a \cdot \sin(\pi b/P) -$$

$$b \cdot \sin(\pi a/P)]\cos\delta\} \cdot \cos(2\pi x/MP + W) -$$

$$t\{a \cdot \sin(\pi b/P) + b \cdot \sin(\pi a/P)\} \cdot \sin\delta \cdot \sin(2\pi x/MP + W)]$$

Simplifying this, we obtain $$P = A(t, \delta, a, b, P) + C(t, \delta, a, b, P) \times \cos(2\pi x/MP + W) + \quad (10)$$

$$S(t, \delta, a, b, P) \times \sin(2\pi x/MP + W)$$

and here A is the component (DC component) which is not dependent on the position x, C the cosine component and S the sine component. Thus, as shown in FIG. 15, the interference pattern 130 is in the ±x directions (in the directions perpendicular to the interference pattern) depending on the values of C ans S.

The amount of phase shift φ [rad] in the intensity distribution of the interference pattern is given by the following equation (11)

$$\tan\phi = S/C = \frac{-t[a\sin(\pi b/P) + b\sin(\pi a/P)] \cdot \sin\delta}{a\sin(\pi a/P) - bt^2\sin(\pi b/P) - t[a\sin(\pi b/P) - b\sin(\pi a/P)] \cdot \cos\delta} \quad (11)$$

Since the period of the light intensity (the period of light and dark fringes) in the interference pattern is the imaging magnification × the pattern pitch P, the amount of shift ΔX of the pattern is given by the following $$\Delta X = MP \times \frac{\phi[rad]}{2\pi} \quad (12)$$

Consequently, it will be seen that the value of φ is determined by measuring the amount of shift ΔX of the interference pattern in the ±x directions and hence the amount of phase shift (π+δ) due to the phase shifters is determined.

Figure 16:
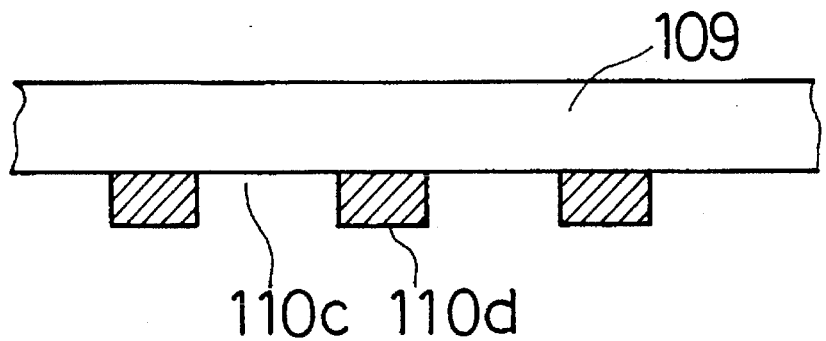
FIG. 16 is a sectional view showing another example of the pattern to be inspected.

The image of the patterns (the interference pattern) of FIG. 14 has such sinusoidal intensity distribution as the pattern image of a reticle in which its phase-shifter deposited portions and non-deposited portions are alternately arranged at a constant pitch as shown in FIG. 16 and in the present embodiment the amount of shift (the phase of the sinusoidal wave) is detected thereby making it possible to effect the measurement with an improved resolution and high degree of accuracy.

Now referring again to FIG. 13, the intensity distribution P in the image of the pattern focused on the detecting means 113 is given by the previously mentioned equation (10) so that the pattern image is caused to shift in the x direction (the direction of pattern arrangement) due to not only the value δ as the amount of phase shift but also the front wave aberration W caused by the defocusing.

For this reason, during the measurement the light shielding member 112a is first removed from the optical path of the −first-order beam $L_m$ and an interference pattern produced by the three light beams or the 0-order beam $L_o$, the +first-order beam $L_p$ and the −first-order beam $L_m$ is focused on the detecting means 113. Then, the contrast of the image is measured while moving the vertically movable stage 114 vertically in the optical axis direction (the Z direction) of the detection optical system 111a, 111b (that is, the detecting means 113 is moved vertically) so that the control circuit 115 searches for a position at which the contrast of the image becomes maximum to determine the best focus position (the best imaging plane of the detection optical system, 111a, 111b). Thereafter, the photosensitive surface of the detecting means 113 is fixed at the best focus position and the −first-order beam $L_m$ is blocked by the light shielding member 112a, thereby detecting the resulting interference image. At this time, the wave front aberration W is reduced to zero and therefore the image is shifted in position only by the amount of phase shift δ due to the phase shifters.

The control circuit 115 analyses the light quantity signals produced from the detecting means 113 on the basis of the intensity distribution in the interference pattern produced by the 0-order beam $L_o$, the +first-order beam $L_p$ and the −first-order beam $L_m$ at the time of determination of the best focus position, thereby determining the amount of shift in the position of the image. In other words, since the intensity distribution in the interference pattern produced by the three light beams of the 0-order beam $L_o$ and the ±first-order beams $L_p$ and $L_m$ takes the form of a substantially a sine wave, by determining the phase difference between it and the intensity distribution in the interference pattern produced by the two light beams of the 0-order beam $L_o$ and the +first-order beam $L_p$ which also takes the form of a sine wave, the amount of shift in the position of the interference pattern corresponding to the amount of phase shift due to the phase shifters (the film thickness of the phase shifter) is determined. Alternatively, it is possible to preliminarily eliminate the 0-order beam $L_o$ by a spatial filter so that the interference pattern produced by the +first-order beam $L_p$ and the −first-order beam $L_m$ is focused at the best focus position and the phase shift is determined on the basis of its intensity distribution. In this case, the intensity distribution serving as the basis also takes the form of a perfect sine wave.

While the description has been made of the case in which the −first-order beam is intercepted, it is possible to block the +first-order beam so that the value of δ is similarly determined by measuring the image produced by the 0-order beam and the −first-order beam. Also, it is possible to measure both of the two cases (the 0-order beam and the +first-order beam as well as the 0-order beam and the −first-order beam) and thereby to average the results obtained. In this case, without determining the intensity distribution which serves as the basis, the measurement of the above-mentioned two cases may be made to determine the phase difference therebetween and thereby determine the value of one half the resulting phase difference as the phase difference corresponding to the amount of phase shift.

As mentioned previously, in FIG. 18 the circuit patterns RP and the pattern to be inspected are formed by the same process and the amounts of phase shift for the two patterns can be considered to be equivalent, with the result that by measuring the amount of phase shift in the inspection pattern in the previously mentioned manner, it is possible to know the amount of phase shift in the circuit patterns RP.

Then, the contrast of the image produced by the interference of the two light beams including the 0-order beam and +first-order beam or the −first-order beam and focused on the detecting means 113 is increased to maximum when the 0-order beam and the ±first-order beams are equal in intensity and it is decreased greatly when the intensities differ greatly. As a result, any pattern to be inspected which is formed to attain an area ratio of 1:1 between the deposited portions of the phase shifters for changing the phase by $\pi$ radians and the non-deposited portions is not suitable as the inspection pattern according to the present invention on the ground that the 0-order beams cancel each other and are not generated.

In order that the intensity ratio may become equal between the 0-order beam and the ±first-order beams, it is suffice if the area ratio between the phase-shifter deposited portions and the non-deposited portions is in the range from about 7:1 to 7:2 or in the range from about 1:7 to 2:7.

Also, as test patterns, those including only phase-shifter deposited portions 110d and non-deposited portions 110c which are alternately arranged as shown in FIG. 16 may be used instead of those which are provided with such chromium films (light shielding patterns) as shown in FIG. 14. Note that the pattern to be inspected can be arranged at any location on the reticle 109. In addition, if such pattern as shown in FIG. 14 or 16 is included in a part of the circuit patterns RP, the part of the circuit patterns RP can be used to effect the same measurement as mentioned previously without especially providing any pattern to be inspected.

Figure 17:
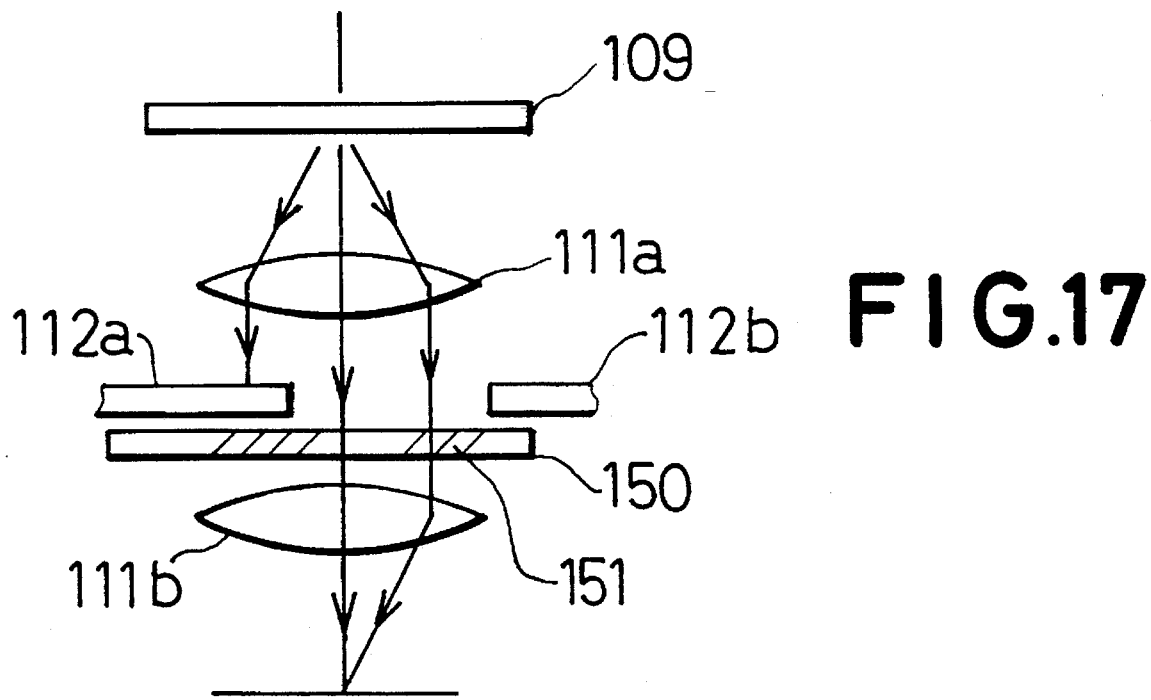
FIG. 17 is an optical path diagram showing another example of the construction of the inspection apparatus shown in FIG. 13.

On the other hand, from the previously mentioned equation (11) it will be seen that the cosine component is decreased as the values of a and b are closer and hence the amount of shift tan $\phi$=S/C of the interference pattern is increased. However, if the values of a and b are made closer to each other, the light quantity of the 0-order beam is decreased and thus the image on the detecting means fails to have a satisfactory contrast. In order to obtain a satisfactory image contrast even under such conditions, as shown in FIG. 17 (the arrangement of the reticle 109, the detection optical systems 111a and 111b and the light shielding members 112a and 112b is the same as in FIG. 1), it is only necessary to insert a spatial filter 150 having a beam attenuating member 151 in the portion corresponding to the optical paths of the ±first-order beams in the vicinity of the Fourier transform plane within the detection optical system 111a, 111b, thereby causing the intensity of the ±first-order beams to approach the intensity of the 0-order beam. With the construction of FIG. 17, the values of a and b in equation (11) can be caused to approach so that the variation of $\phi$ with the variation of $\delta$ is increased, thereby making it possible to measure the amount of phase shift with greater accuracy.

It is to be noted that in the above-mentioned embodiment the pitch of the pattern to be inspected can be selected arbitrarily.

Also, while, in the above embodiment, the aperture stop 106 is not mentioned particularily, it is only necessary to adjust the aperture stop 106 in such a manner that the 0-order beam and the ±first-order beams from the pattern to be inspected are separated from one another in the vicinity of the Fourier transform plane within the detection optical system 111a, 111b. In this case, it is only necessary to select the numerical aperture of the aperture stop 106 less than the numerical aperture ($\lambda$/2P) of the illumination optical system (101 to 108).

Further, while the size, shape, etc., of the illumination area of the light beam L3 on the reticle 109 may be fixed as in the above-described embodiment, since the diffracted light and the scattered light from other patterns than the inspection pattern TP can fall on the detecting means 113, it is preferable that a field stop is arranged in a plane which is conjugate with the reticle 109 and its light transmission opening is made variable in accordance with the size and shape of the pattern to be inspected.

Further, while, in the above-described embodiment, the 0-order beam and the ±first-order beams are blocked by the light shielding members 112a and 112b, it is possible to construct so that as for example, a plurality of different spatial filters (light shielding members) are prepared in correspondence to the Fourier transform patterns of the pattern to be inspected (namely, the positions and sizes of the 0-order beam and the ±first-order beams at the Fourier transform plane and the spatial filters are interchangeably inserted in the vicinity of the Fourier transform plane within the detection optical system, and all the same effect as the previously mentioned light shielding members 112a and 112b can be obtained. Further, liquid crystal devices, electrochromic devices or the like may be used as light shielding means and in this case there is an advantage that the 0-order beams and the ±first-order beams can be extracted easily even if the pitch of the pattern, the illumination conditions, etc., are changed. At this time, it is possible to adjust the light transmittance of those portions through which the ±first-order beams are passed so that the light shielding members serve the function of the previously mentioned spatial filter 150 (FIG. 17).

Here, a reticle to be inspected may be of any type provided that it is formed with phase shifters and it may be a phase-shifted reticle of the spatial frequency modulation type, edge enhancement type or light shielding effect enhancement type or a reticle composed of phase-shifter (dielectric film) deposited portions and non-deposited portions (reticle bare portions). It is to be noted that when the edge enhancement type or the light shielding effect enhancement type is used, it is desirable to prepare a pattern to be inspected in addition to circuit patterns as in the case of the previously mentioned embodiment reticle.

Figure 19:
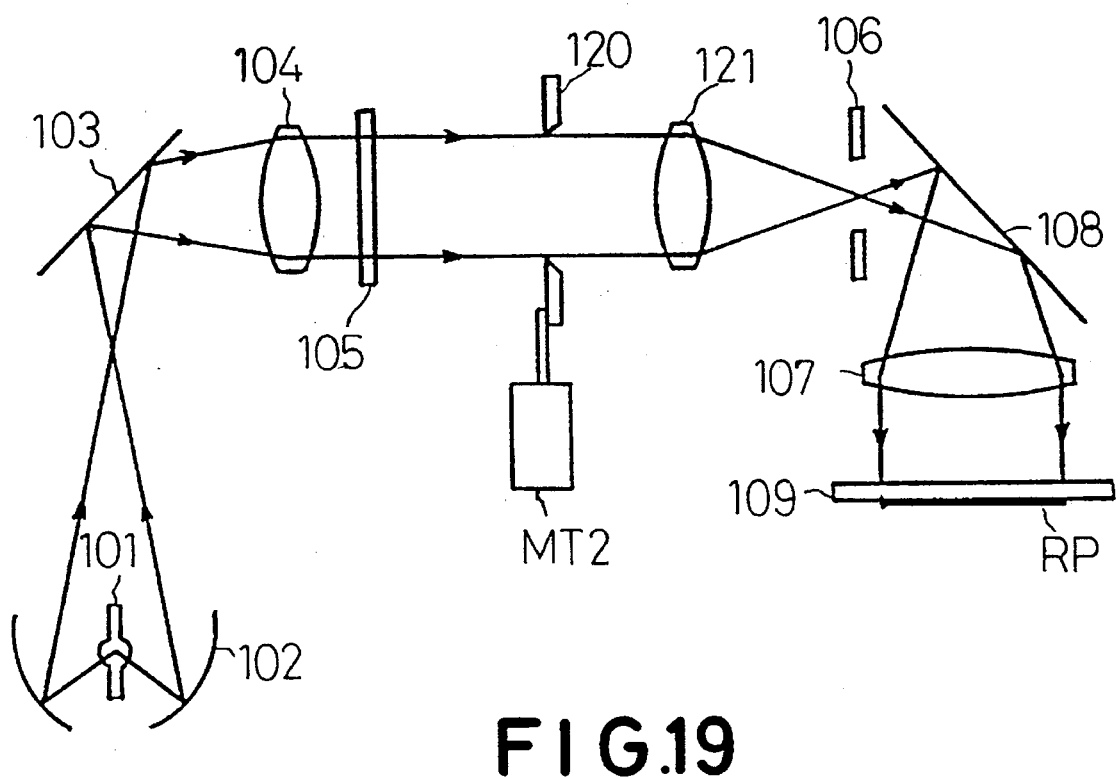
FIG. 19 is a schematic diagram showing the construction of the illumination optical system employing the Köhler's illumination.

Also, while, in the previously mentioned embodiment, the stage RS is driven so as to place the pattern to be inspected within the illuminating area of the light beam L3, by arranging for example a variable blind (field stop) in a plane which is substantially conjugate with the reticle 109, it is possible to accurately illuminate the pattern to be inspected with the light beam L3 without moving the reticle 109. It is needless to say that where the pattern to be inspected is arranged at the end of the reticle 109, for example, tha pattern image produced by the detection optical system 111a, 111b shifts traversely and therefore the detecting means 113 must be correspondingly moved within the horizontal plane. FIG. 19 is a schematic diagram showing the construction of an illumination optical system employing the Köhler's illumination and those component parts performing the same operations and functions as in the apparatus shown in FIG. 13 are respectively designated by the same reference numerals. In FIG. 19, a relay lens system 121 is added to effect the Köhler's illumination. In addition, an aperture stop 120 is driven by a motor $MT_2$ thereby selecting any given illumination area on the reticle 109.

While the present invention has been described as applied to the reticle inspection apparatus, it is possible to provide a projection exposure apparatus (stepper) with the above-mentioned inspection function. More specifically, by arranging light shielding means near the Fourier transform plane within the projection optical system of the exposure apparatus and employing an illuminometer (photodiode) arranged on the wafer stage, it is possible to determine the amount of phase shift (or film thickness) of the phase shifters by the same operation as the above-mentioned embodiment.

Embodiment 3

Figure 20:
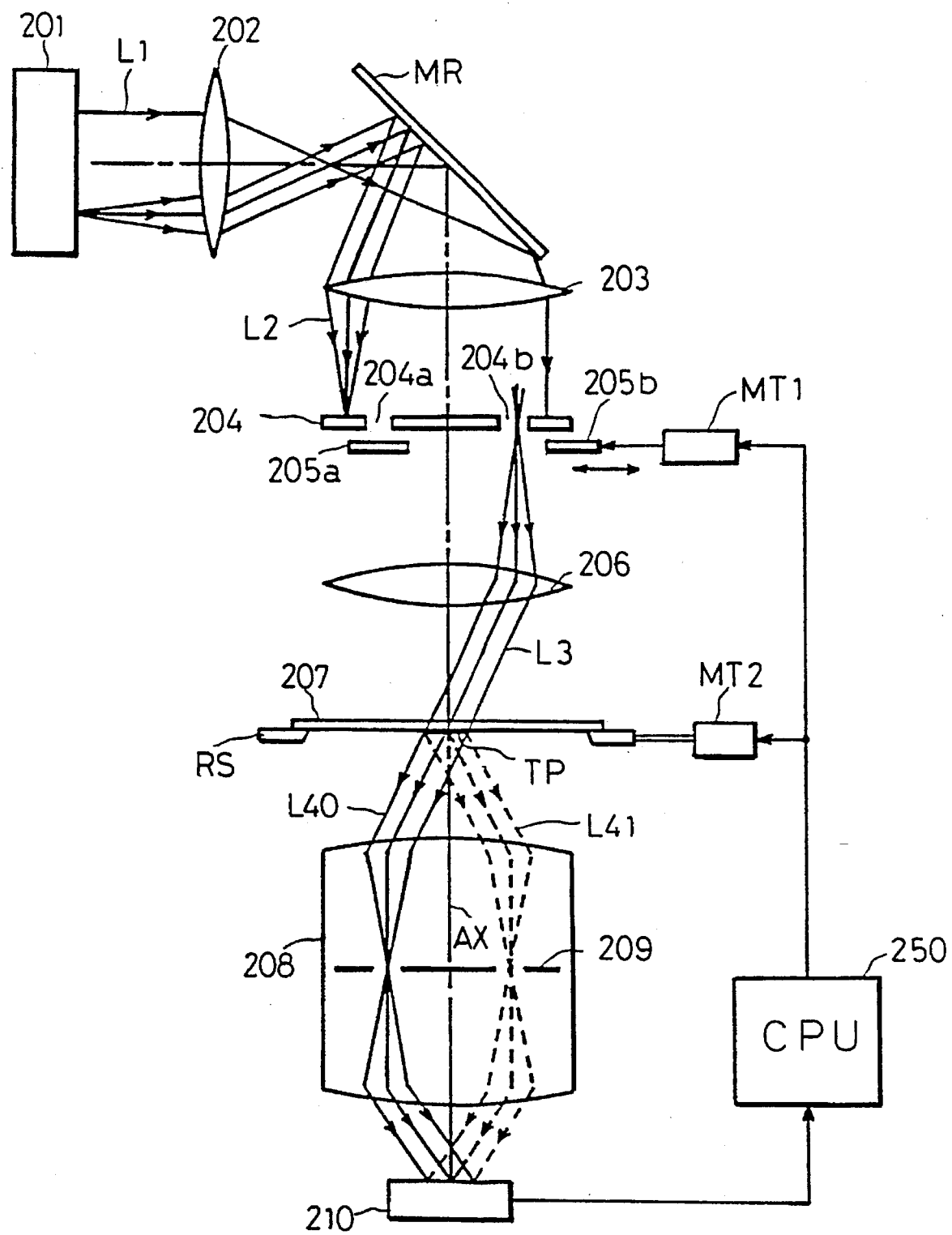
FIG. 20 is an optical path diagram showing the construction of a third embodiment of the present invention.

Referring to FIG. 20, there is illustrated the construction of an inspection apparatus according to a third embodiment of the present invention.

The inspection apparatus of this embodiment includes a light source 201, an illumination optical system (relay lenses 202 and 203, a mirror MR and a condenser lens 206), an inspection optical system 208 and a position detector 210, and the illumination optical system and the inspection optical system 28 are arranged in a manner that their optical axes are aligned on the same axis. A reticle 207 to be inspected is held vertically with respect to the optical axis between the illumination optical system and the inspection optical system 28, and the position detector 210 is arranged so that its photosensitive surface is positioned in the vicinity of the imaging plane of the inspection optical system 208. Also, arranged in the vicinity of the Fourier transform plane within the illumination optical system (i.e., the plane on which the Fraunhofer diffraction pattern of the inspection pattern on the reticle 207 is formed and its conjugate plane) is a spatial filter 204 including light transmitting portions 204a and 204b arranged at a position corresponding to ½ of the fundamental period at the time of the Fourier transformation of the pattern to be inspection and at its vicinity. The light transmitting portions 204a and 204b are respectively provided with slide-type shutters 205a and 205b so that the light transmitting portions 204a and 204b can be opened simultaneously or only one of them can be opened by means of the motor $MT_1$. In the Figure, the light transmitting portion 204a is closed by the shutter 205a.

With the apparatus described above, the beam of light L1 emitted from the light source 201 is a monochromatic light having substantially the same wavelength as the exposure light wavelength when the phase-shifted reticle 207 is actually used in the lithographic operation and it reaches the spatial filter 204 through the relay lenses 202 and 203 and the mirror MR (the light beam L2 in the Figure). Since the spatial filter 204 blocks the illuminating light L2 at other portions than the light transmitting portions 204a and 204b, the light quantity distribution at the Fourier transform plane within the illumination optical system is such that the light quantity is reduced at the portions other than the point corresponding to ½ of the fundamental period at the time of the Fourier transformation of the pattern to be inspected and its vicinity. In FIG. 20, the shutter 205a is closed so that only the illuminating light L2 incident on the light transmitting portion 204b is projected onto the reticle 207 through the condenser lens 206.

Figure 21:
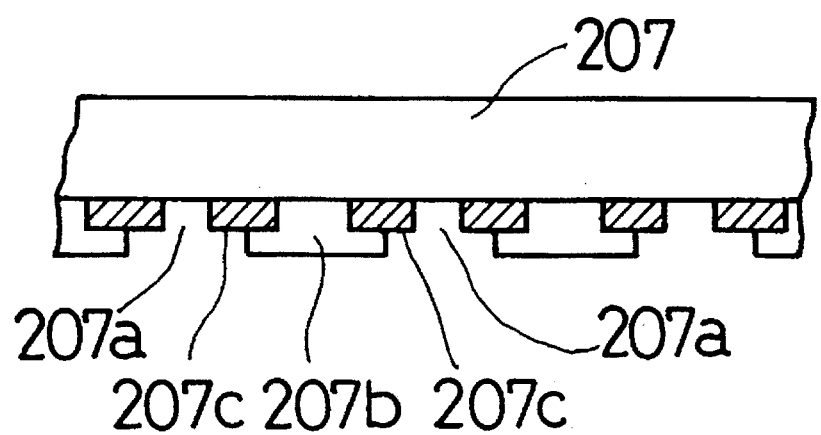
FIG. 21 is a schematic sectional view showing an example of the pattern to be inspected according to the third embodiment of the present invention.

Referring now to FIG. 21, there is illustrated a sectional view of an inspection pattern TP formed on the reticle 207 and, as in the case of the Embodiment 2 (FIG. 14), a periodic construction is formed in which the basic unit composed of a phase-shifter non-deposited portion 207a, a chromium film 207c, a phase-shifter deposited portion 207b and a chromium film 207c is repeated. At this time, if the fundamental period of the pattern is represented as P (the distance to the non-deposited portion 207b), the optical Fourier transformed positions of the fundamental period become $\pm\lambda/P$ ($\lambda$ is the wavelength of the illuminating light). Thus, where the pattern as shown in FIG. 21 is to be inspected, the light transmitting portions 204a and 204b of the spatial filter 204 are disposed centering those points which are apart from the optical axis of the illumination optical system by $\pm\frac{1}{2}\cdot f\lambda/P$ (f represents the focal length of the condenser lens 206).

Then, the reticle 207 is mounted on the stage RS which is movable two-dimensionally within the horizonal plane by a motor $MT_2$ and the inspection pattern TP is set within the illumination area of the illuminating light L3 prior to inspection. The 0-order diffracted beam L40 and the +first-order diffracted beam L41 of the illuminating light L3 from the inspection pattern TP are entered into the inspection optical system 208 so that the beams are once condenced into spots at the Fourier transform plane within the system and the spots are passed substantially symmetrically with the optical axis AX, thereby focusing at the surface of the position detector 210.

The method of determining an error in the amount of phase shift according to the present embodiment will now be described. With the inspection pattern TP of the reticle 209, if a represents the width of the phase-shifter non-deposited portions 207a, b the width of the deposited portions 207b, P the pattern repetition period, ($\lambda+\delta$) the amount of phase shift due to the phase shifters, 1 the amplitude transmittance of the non-deposited portions 207A, and t·exp(iδ) the amplitude transmittance of the deposited portions 207b with ($0 \leq t \leq 1$), the amplitudes of the 0-order diffracted beam and the ±first-order diffracted beams generated from the pattern are given as relative values by the previously mentioned expression (6).

In FIG. 20, the illumination light L3 passed through the transmitting portion 204b illuminates the reticle 207 through the condenser lens 206 with an inclination with respect to the optical axis. The angle formed by the illuminating light L3 and the optical axis is determined by the position of the light transmitting portion 204b of the spatial filter 204. Since the light transmitting portion 204b is provided at the intermediary point between the Fourier transform position of the fundamental period of the pattern formed on the reticle 207 and the optical axis, the angle formed by the illuminating light L3 and the optical axis is one half the angles formed by the directions in which the ±first-order diffracted beams are generated when the illuminating light falls vertically on the reticle 207 and the optical axis. Thus, as shown in FIG. 20, the direction of the illuminating light L3 reaching the reticle 207 from the transmitting portion 204b becomes the −½ order direction of that obtained when the illuminating light falls vertically on the reticle 207. Contrary to the case of the Figure, if the shutter 205a is opened so that the beam reaches the reticle 207 from the light transmitting portion 204a, this direction becomes the +½ order direction.

As shown in the Figure, when the reticle 207 is illuminated by the illuminating light L3 with the inclination of the −½ order direction, the 0-order diffracted beam L40 from the pattern to be inspected travels straightforward and generated in the −½ order direction. Also, the +first-order diffracted beam L41 is generated in the (−½+1) order =½ order direction and the −first-order diffracted beam is generated in the (−½−1)=−3/2 order direction.

Then, since the directions in which the first-order diffracted beams are generated are determined by $\lambda/P$ ($\lambda$=the wavelength of the illuminating light), if the pattern pitch P is reduced or the aperture of the inspection optical system 208 is small, the beams of the ±½ order directions are transmitted through the inspection optical system 208 and the beams of the ±3/2 order directions do not fall on the inspection optical system 208. At this time, the 0-order diffracted beam L40 and the +first-order diffracted beam L41, which are condensed by the inspection optical system 208, reach the photosensitive surface of the position detector 210 which is at the position of the pattern imaging plane by the inspection optical system 208 and an interference pattern due to the interference of the two beams appears.

Figure 15B:
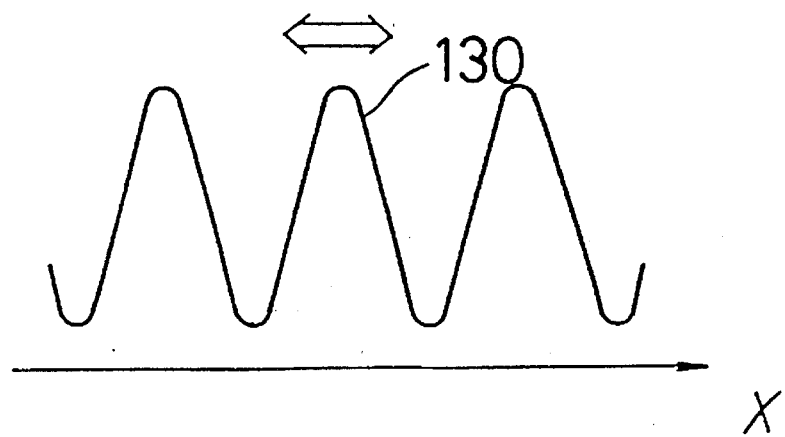

If the imaging magnification between the pattern surface of the reticle 207 and the position detector 210 is M times, the intensity distribution P in the interference pattern is given by equation (9) (simplified into equation (10)) as in the case of the Embodiment 2. As a result, even in this embodiment the interference pattern is moved in the ±x direction (the directions transversing the interference pattern) as shown in FIG. 15B in dependence on the values of C ans S in equation (10). In other words, by measuring the amount of shift $\Delta x$ of the interference pattern by the position detector 210, the amount of phase shift $\delta$ by the phase shifters is determined.

Next, the method of determining the reference (origin) for measuring the amount of pattern shift $\Delta x$ will be explained. Apart from the above-mentioned measurement effected by closing the light transmitting portion 204a by the shutter 205a and opening the light transmitting portion 204b in the spatial filter 204 of FIG. 20, when the measurement is effected again by opening the light transmitting portion 204a and closing the light transmitting portion 204b, the interference pattern is now moved in the negative direction and its amount of movement is measured as $-\Delta x$. Therefore, if the measurement with only the light transmitting portion 204a opened and the measurement with only the light transmitting portion 204b opened are separately effected and the difference in position between the resulting images is determined, there results $2\Delta x$. In other words, in accordance with this value the amount of phase shift due to the phase shifter films can be determined. If the energy transmittance=$t^2$ of the phase shifters is known, it is also possible to determine the amount of phase shift of that phase shifter whose transmittance is not 100%.

Alternatively, with both of the light transmitting portions 204a and 204b of the spatial filter 204 being opened, the measurements using simultaneously the beams from the two light transmitting portions can be effected to determine the reference point. In this case, the amount of shift of the pattern produced by the light from the light transmitting portion 204a and the amount of shift produced by the light from the light transmitting portion 204b cancel each other so that the amount of shift $\Delta x$ of the pattern is reduced to zero and this position is selected as the origion of $\Delta x$.

The measurement of the position of the interference pattern can be easily effected from a plurality of the peak positions in a restrictive intensity distribution or by measuring the coordinates of a plurality of the positions having a specified intensity. It is to be noted that since the −first-order diffracted beam and the second and higher order diffracted beams from the inspection pattern TP can enter the inspection optical system 208 due to the pitch, duty cycle or the like of the pattern TP to be inspected, as shown in FIG. 20, it is desirable to arrange a spatial filter 209 capable of selectively extracting the 0-order and first-order diffracted beams in the vicinity of the Fourier transform plane within the inspection optical system 208.

After the position of the image of the pattern has been measured with the shutter 205a being closed and the shutter 205b being opened as mentioned previously, a control circuit 250 first measures the position of the image of the pattern with the shutter 205b being opened through the motor $MT_1$ and then the control circuit 250 effects the similar measurement with the shutter 205a being opened and the shutter 205b being closed through the motor $MT_1$. In accordance with the difference $2\Delta A x$ between the position of the image when opening only the shutter 205a and the position of the image when opening only the shutter 205b, the phase shift $\phi$ in the intensity distribution of the image is determined from the previously mentioned equation (12) and hence the amount of phase shift $\delta$ due to the phase shifter films is determined from equation (11).

Also, after the measurement has been effected with only the shutter 205b being opened, the measurement may be effected with both of the shutters 205a and 205b being opened; in this case, the difference in position between the images of the two measurements is $\Delta x$ and the amount of phase shift $\delta$ can be similarly determined.

Then, as will be seen from the optical path diagram of FIG. 20, in the present embodiment the 0-order diffracted beam and the first-order diffracted beam from the pattern on the reticle pass through the optical paths which are symmetric with the optical axis of the inspection optical system 208. As a result, the position of the interference pattern is not varied due to the wave front aberration caused by the shift (defocusing) of the position detecting means from the imaging plane, the spherical aberration of the inspection optical system, etc., and moreover the depth of focus is great, thereby eliminating the need to exactly align the position detector with the best imaging plane of the inspection optical system 208. Also, where the focusing is to be performed, it is only necessary that the shutters 205a and 205b are both opened and the contrast of the pattern image is measured while vertically moving the position detector 210 along the optical axis AX, thereby determining the position of the maximum contrast as the best focus position (the best imaging plane).

Embodiment 4

Figure 22:
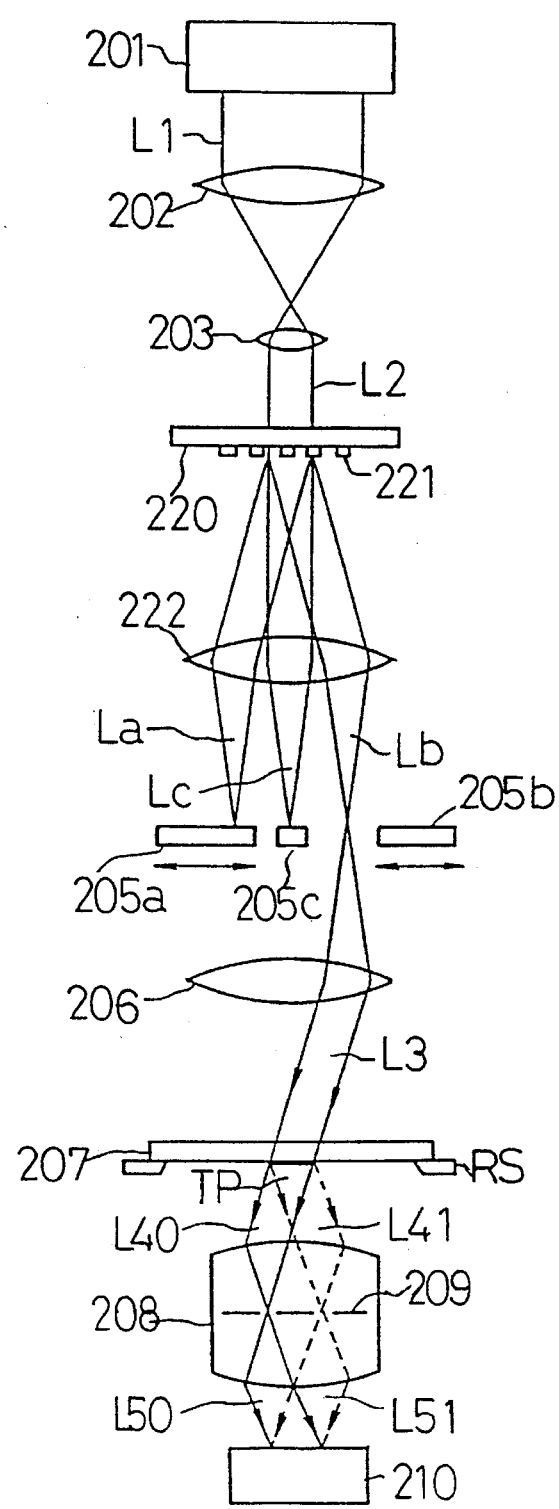
FIG. 22 is an optical path diagram shwoing the construction of a fourth embodiment of the present invention.

Referring now to FIG. 22, there is illustrated an optical path diagram showing the construction of an inspection apparatus according to a fourth embodiment of the present invention. In the Figure, the light beam L1 produced from a light source 201, which emits a monochromatic or quasi-monochromatic light, is reshaped by relay lenses 202 and 203 to illuminate a grooved transparent flat sheet 220 of a diffraction grating 221. The diffraction grating 221 may be made of a light shielding material such as chromium or it may be made of dielectric films which give a phase difference.

The 0-order diffracted beam Lc, the −first-order diffracted beam La and the +first-order diffracted beam Lb from the diffraction grating 221 are condensed at a point on the optical axis and points corresponding to ⅓ of the fundamental period of the pattern TP to be inspected in the Fourier transform plane of the illumination optical system (the relay lenses 202 and 203 and the condenser lens 206) through the relay lenses 222.

In the Fourier transform plane within the illumination optical system, shutters 205a, 205b and 205c are respectively arranged at the positions corresponding to the condensing points of the −first-order diffracted beam, the +first-order diffracted beam and the 0-order diffracted beam from the diffracting grating 221. In the present embodiment, beam deflecting means is formed by the diffraction grating 221, the relay lense 222 and the shutters 205a, 205b and 205c.

In the present embodiment, the light beams along the optical axis of the illumination optical system, i.e., the 0-order diffracted beams Lc are not desired so that the shutter 205c is always in a light shielding condition and the shutters 205a and 205b are adapted to be opened and closed. FIG. 22 shows the condition in which the shutter 205a on the optical path of the −first-order diffracted beam La is closed and and the shutter 205b on the optical path of the +first-order diffracted beam Lb is opened. As a result, in the case of the Figure, only the +first-order diffracted beam Lb is directed to the reticle 207 through the condenser lense 206 and it illuminates a pattern PT to be inspected. At this time, while the diffracted beams of the respective orders are produced from the pattern TP to be inspected, as in the case of the first embodiment, the illuminating light L3 illuminates the reticle 207 from the −½ order direction and thus only the 0-order diffracted beam L40 and the first-order diffracted beam L41 fall on the inspection optical system 208 (its optical axis is aligned with the optical axis of the illumination optical system). Then, an image of the pattern produced by the two beams or the 0-order diffracted beam L40 and the first-order diffracted beam L41 is focused on the photosensitive surface of the position detector 210.

In FIG. 22, the Fourier transform plane of the inspection pattern TP at which the shutters 205a, 205b and 205c are arranged is also the Fourier transform plane of the diffraction grating 221 and therefore it is at a position which is in imaging relation with the reticle 207. If the imaging magnification between the diffraction grating 221 and the reticle 207 is N times, it is only necessary to select the pitch of the diffracting grating 221 to be 2P/N (P represents the pitch of the inspection pattern PT on the reticle 207).

As in the case of the third embodiment, the measurement of the amount of phase shift is effected in such a manner that in the condition of FIG. 22 the position of the image on the position detector 210 is measured first and then, with the shutter 205b closed and the shutter 205a opened, the position of the image on the imaging plane is measured again, thereby determining the value of $\delta$ from the difference $2\Delta x$ between the measurements.

Embodiment 5

Figure 23:
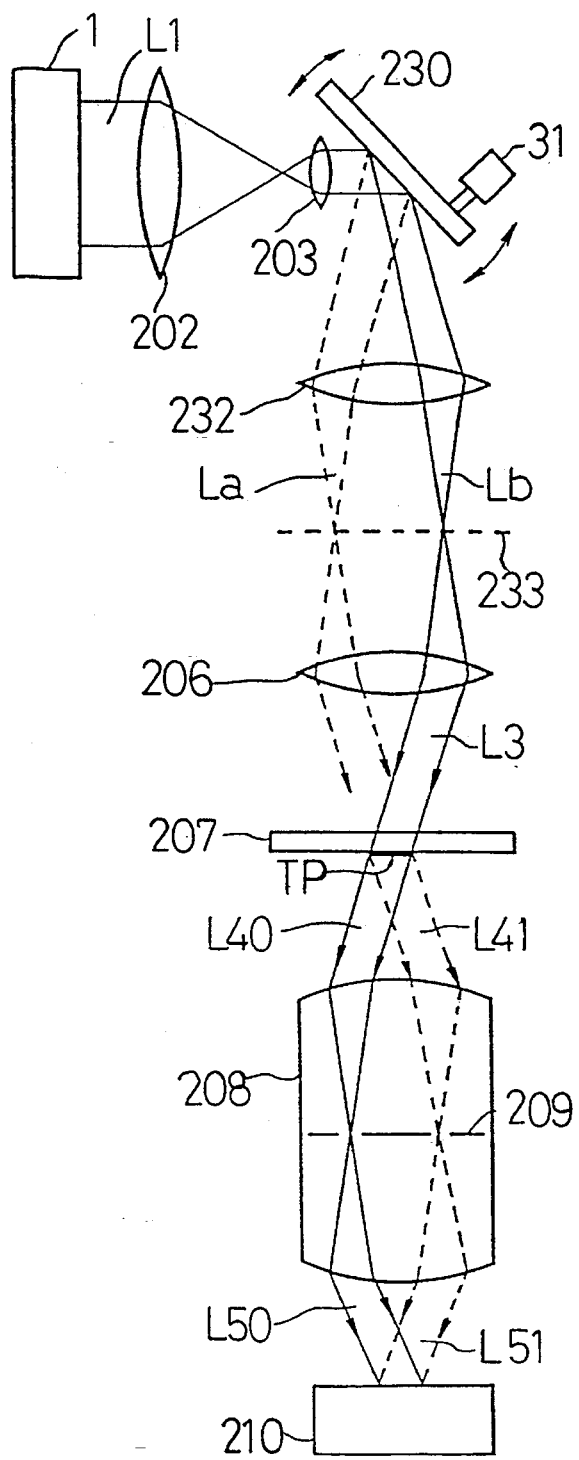
FIG. 23 is an optical path diagram showing the construction of a fifth embodiment of the present invention.

Referring now to FIG. 23, there is illustrated an optical path diagram showing the construction of an inspection apparatus according to a fifth embodiment of the present invention.

In the Figure, the illuminating light L1 emerging from a light source 201 which emits a monochromatic light or quasi-monochromatic light, is reshaped by relay lenses 202 and 203 and it is reflected by a movable mirror (vibration mirror) 230. The movable mirror 230 is rotatable about the axis vertical to the plane of the paper and it is rotated by an active member 31 such as a motor or piezoelectric element. The reflected beams La and Lb from the movable mirror 230 are shifted in the directions parallel to the plane of the paper by the rotation of the movable mirror 230. In FIG. 23, the reflected beams are at the position of Lb on the right side of the optical axis in the Figure. Also, the movable mirror 230 may be provided with an additional axis of rotation so that the reflected beams are shifted in the vertical directions to the plane of the paper by the movable mirror 230 and the active member 31.

The movable mirror 230 is adjusted so that the positions of the reflected beams La and Lb at a Fourier transform plane 233 of an inspection pattern with respect to a condenser lense 206 become the middle points (two points) between the Fourier transform position of the fundamental period of the inspection pattern TP as in the case of the third and fourth embodiments. In FIG. 23, the mirror 230 is adjusted so that the reflected beam Lb condensed at the middle point between the −first-order diffracted beam corresponding point on the right side of the paper plane and the optical axis through a lense 232.

In this condition, a reticle 207 is illuminated by an illuminating light L3 having an inclination of −½ order direction so that only the first-order diffracted beam L41 of the inspection pattern TP is directed to an inspection optical system 208 having the same optical axis as the illumination optical system and an image of the pattern is focused on a position detector 210 (L50 and L51 respectively designate the 0-order diffracted beam and the +first-order diffracted beam which are passed through the inspection optical system 208).

With this inspection apparatus, the amount of shift of the image of the pattern is detected in such a manner that after the position of the image by the 0-order diffracted beam L50 and the +first order diffracted beam L51 has been detected, the reflecting mirror 230 is adjusted so that the reflected beam La is condensed at the other middle point between the pattern fundamental period corresponding point and the optical axis (the middle point between the +first-order diffracted beam corresponding point and the optical axis) and the position of the interference pattern is measured again. The amount of phase shift $\delta$ due to the phase shifter films is determined in accordance with the difference, $2\Delta x$, between the two measurements.

As in the case of the embodiment shown in FIG. 23, instead of using light shielding means such as a spatial filter as beam deflecting means within the illumination optical system, it is possible to condense the whole illumination at a given position in the Fourier transform plane within the illumination optical system so that the loss of the illuminating light quantity is reduced and the intensity of the image detected by the position detector 210 is increased, thereby measuring the amount of shift of the image with greater accuracy.

Embodiment 6

FIGS. 24 and 25 show respectively the constructions of an inspection apparatus according to a sixth embodiment and its modification. It is to be noted that the construction on the side of the reticle 207 from its Fourier transform plane (the pupil plane within the illumination optical system) 233 is identical with the fifth embodiment shown in FIG. 23. Also, in FIGS. 24 and 25 the component parts which are identical in operation and function as those of the fifth embodiment (FIG. 23) are designated by the same reference numerals.

In FIG. 24, the illuminating light L1 emitted from the light source 201 is projected through the relay lenses 202 and 203 to a lens system 240 having a positive power and a lens system 241 having a negative power. The lens systems 240 and 241 are arranged in a plane which is conjugate with the reticle 207. Also, the sum of the powers of the lens systems 240 and 241 is zero. The lens systems 240 and 241 are respectively movable through lens drivers 242 and 243 within a plane substantially perpendicular to an optical axis AX' of the illumination optical system. The illuminating light beam transmitted through the lens systems 240 and 241 is converted to a light beam including a principal ray which is different from the optical axis AX' and it is condensed into a spot form at a position in the Fourier transform plane 233 which is different from the optical axis AX' through the lens system 232. Note that the construction on the reticle 207 side from the Fourier transform plane 233 is the same as the fifth embodiment.

Then in FIG. 24, the lens systems 240 and 241 are moved in the opposite directions by substantially the same distance relative to the optical axis AX' within the plane of the paper. As a result, the light beam transmitted through the lens systems 240 and 241 enters the lens system 232 with a given angle of inclination with respect to the optical axis AX'. Thus, by adjusting the positions of the lens systems 240 and 241 by the lens drivers 242 and 243, it is possible to direct the emitted light beam to any arbitrary direction. Note that the lens drivers 242 and 243 are controlled by a control circuit 250.

Also, it is possible to construct such that a separate lens system having a positive power and adapted to be moved by a separate driver is newly provided on the reticle 207 side from the lens system 241 and the sum of the powers of the lens systems 240 and 241 and the newly added separate lens system of the positive power becomes zero. Similarly, it is possible to construct such that a lens system having a negative power is provided on the light source 1 side from the lens system 240 and the sum of the lens systems 240 and 241 and the newly added negative lens system becomes zero.

It is to be noted that the construction of the lens systems movable relative to the optical axis AX' is not limited to the above-mentioned combinations and it is possible to use any construction provided that it comprises a lens group composed of a plurality of lens elements such that the sum of the powers of the lens systems becomes zero and the illuminating light beam is directed to any arbitrary direction through the driving of the lens elements. Also, there is no limitation to the driven lens elements and similarly they may be of any lens elements which are capable of directing the illuminating light beam to any arbitrary direction.

On the other hand, in FIG. 25 the illuminating light L1 emitted from the light source 201 is first condensed on the lens system 202 and then it enters transmitting means 245 such as optical fiber. Where the reticle 207 is the object plane, the emitting end of the light transmitting means 245 is arranged in the pupil plane of the illuminating optical system or the Fourier transform plane 233 of the reticle 207. Also, the emitting end of the light transmitting means 245 is movable within a plane substantially perpendicular to the optical axis AX' of the illumination optical system by a driver 244 thereby distributing the illuminating light beam to any given positions within the Fourier transform plane of the illuminating light beam. As a result, the light beam emitted from the light transmitting means 245 is converted to a collimated light beam by the lens system 206 and then projected onto the reticle 207 at a given angle of inclination. Note that the construction on the reticle 207 side from the Fourier transform plane 233 is the same as the fifth embodiment and the driver 244 is controlled by the control circuit 250 as in the fifth embodiment.

With the above-described third to sixth embodiments, it is desirable to select the ratio of the numerical aperture of the illumination optical system to the numerical aperture of the inspection optical system 208 (or the so-called σ value) to be about 0.2 or less, for example.

On the other hand, the contrast of the pattern image produced by the interference of the two beams or the 0-order diffracted beam and the +first-order or −first-order diffracted beam is the maximum when the 0-order beam and the first-order beam are equal in intensity and it is decreased considerably when the two intensities are different greatly. Thus, if the area ratio between the phase shifter films and the mask bare portions in the pattern to be inspected is 1:1, the 0-order beams cancel each other and practically they are not produced. Then, in order that the intensity ratio between the 0-order beam and the first-order beam may be substantially equal, it is desirable that the above-mentioned area ratio in the pattern to be inspected is in the range from about 7:1 to 7:2 or in the range from about 1:7 to 2:7.

Further, it will be seen that as the values of a and b become closer in the previously mentioned equation (11), the cosine component is decreased and hence the amount of phase shift of the interference pattern or $\tan\phi = S/c$ is increased. However, if the values of a and b are made closer, the light quantity of the 0-order beams is decreased and the pattern image on the position detector 210 fails to have a satisfactory contrast. In order to obtain a satisfactory contrast under such conditions, it is only necessary to arrange a light attenuating filter in the vicinity of the Fourier transform plane within the inspection optical system 208 to cause the intensity of the first-order diffracted beam to approach that of the 0-order beam. As a result, the values of a and b in the above equation (11) can be made closer with the result that the variation of $\phi$ is increased with the variation of $\delta$ and the amount of phase shift is measured with excellent accuracy. In this case, there is the possibility that the first-order diffracted beam is shifted in phase with respect to the 0-order beam as it is transmitted through the light attenuating filter and therefore the light attenuating filter should preferably be arranged in a manner that the phase difference between the two beams becomes $2n\pi$ (n is an integer). Note that a dielectric multi-layer film of high reflectance may for example be used as the light attenuating filter.

Further, in the case of the third embodiment, if the pitch of the pattern TP to be inspected is changed, the size and position of the openings of the light transmitting portions in the spatial filter 204 arranged within the pupil plane of the illumination optical system are also changed and therefore it is desirable to construct so that as for example, a plurality of different spatial filters are preliminarily prepared in correspondence to the Fourier transformed patterns of the inspection patterns TB thereby interchangeably inserting the spatial filters into the pupil plane. Still further, a liquid crystal device, an electrochromic device or the like may be used as the spatial filter 204 and in this case there is the advantage that the angle of incidence of the illuminating light beam L3 to the reticle 207 can be easily changed by electrically adjusting the position and size of the light transmitting portions in accordance for example with the change in the pitch of the inspection pattern TP. In this case, it is possible to adjust the light transmittance of the light transmitting portions in the spatial filter 204 so that the spatial filter 204 within the illumination optical system simultaneously serves the function of the previously mentioned light attenuating filter (e.g., the filter 150 shown in FIG. 17).

In the above-mentioned third to sixth embodiments, the light source 201 may be a laser light source, a combination of an incandescent lamp, e.g., a tungsten lamp and a band-pass filter or a combination of a bright line lamp, e.g., a mercury vapor lamp and a band-pass filter or an interference filter. The illuminating light is a monochromatic light or a quasi-monochromatic light of substantially the same wavelength as the exposure light wavelength when the phase-shifted reticle is used in the actual lithographic operation. For example, where both of a phase-shifted reticle for the i line (360 nm) of the mercury vapor lamp and a phase-shifted reticle for the g line (436 nm) of the mercury vapor lamp must be inspected, it is only necessary that the light source 201 is composed of a combination of the mercury vapor lamp and a band-pass filter and the band-pass filter is changed in accordance with the kind of the phase-shifted reticle (for the i line or the g line).

Also, where a phase-shifted reticle for the KrF laser is to be inspected, it is only necessary that beside the previously mentioned mercury lamp light source, a KrF laser light source or a light source composed of a combination of a xenon mercury lamp and a band-pass filter is provided so that the light sources are selectively used in accordance with the kind of a reticle. Note that at this time, it is assumed that the various optical members of these embodiments are selectively subjected to aberration compensation for the various wavelengths used.

In the respective embodiments, the position detector 210 may be composed of an image pickup device of the CCD type or a combination of an image pickup tube and a signal processing circuit or alternatively it may be of such type that a light quantity sensor having one or more transmission slits relatively scans in a direction perpendicular to the interference pattern generated (the image of a pattern to be inspected) so that its light quantity distribution is measured and its position is measured by a processing circuit. Note that the spacing of the plurality of transmission slits should preferably be the same as the pitch of the interference fringes. In addition, the imaging magnification of the inspection optical system 208 should preferably be of a magnification type so that the pattern on the reticle 207 is magnified and projected onto the position detector 210.

While, in the foregoing description, the illuminating light beam L3 for illuminating the reticle 207 is shown as inclined relative to the optical axis within the plane parallel to the plane of the paper for purposes of facilitating the understanding of the Figure, this is due to the fact that the pattern TP on the reticle 207 is assumed to have been arranged perpendicularly to the plane of the paper as shown in FIG. 21 and it is needless to say that the light beam L3 for illuminating the reticle 207 may possibly be inclined in a direction perpendicular to the plane of the paper if the inspection pattern is arranged in any other direction. Note that at this time, by rotating relative to the optical axis the spatial filter 204 and the shutters 205a and 205b in the case of the third embodiment and the patterned transparent flat sheet 220 of the diffraction grating 221 and the shutters 205a and 205b in the case of the fourth embodiment, it is possible to cope with the inspection patterns having any arbitrary direction. In the case of the fifth embodiment, it is only necessary to selectively rotate the movable mirror 230 about the two axes of rotation as mentioned previously.

Also, the inspection pattern shown in FIG. 21 represents only one example and the construction of FIG. 21 may for example be modified so that the pattern is composed of only the non-deposited portions 207a and the deposited portions 207b without the chromium films 207c. Also, the energy transmittance of the non-deposited portions 207b may have any arbitrary value. However, as shown by equation (11), the measurement of the amount of phase shift $\delta$ is influenced by the energy transmittance $t^2$ and its square root t ($0 \leq t \leq 1$, real number), the value of $t^2$ must be known. While the value of $t^2$ may be measured by use of a separate measuring device, it is possible to form uniform opening patterns and uniform phase-shifter film patterns (the energy transmittance=$t^2$) on the reticle 207 so that the light quantity ratio between the two patterns is measured by the inspection apparatus of the present invention to thereby obtain the value of $t^2$ from the resulting value. Even if the illuminating light L3 is projected onto the uniform opening patterns or the uniform phase-shifter film patterns, as in the case of the previously mentioned embodiment, no +first-order diffracted beam L41 is produced and only the 0-order diffracted beams (transmitted beams) L40 reach the position detector 210. The uniform openings are first illuminated by the illuminating light L3 to determine the then current light quantity on the position detector $210=E_0$ and then the uniform phase-shifter film patterns are illuminated by the illuminating light L3 to determine the light quantity on the position detector $210=E_1$. From this we obtain $t^2=E_1/E_0$.

The function of calculating $t^2=E_1/E_0$ may be incorporated in the position detector 210 or alternatively a computing unit connected to the position detector 210 by electric signals may be provided. Note that this computing unit may be used to determine the value of $\delta$ from the values of $\Delta x$ and $t^2$ in accordance with equations (11) and (12).

While the pattern to be inspected may be incorporated as the exclusive inspection pattern in the reticle 207, a suitable pattern may be selected from the circuit patterns on the reticle 207 for use as the pattern to be inspected. Also, the pitch, duty cycle, etc., of the inspection pattern can be selected arbitrarily. It is desirable that the mechanical members holding the reticle 207 should preferably be movable in a plane vertical to the optical axes of the inspection optical system and the illumination optical system so as to be able to inspect the inspection pattern at any given position on the reticle 207.

What is claimed is:

1. A method of inspecting a phase-shifted mask including at least one phase shifter adapted to change the phase of light and selectively deposited in correspondence to a desired pattern configuration, said method comprising the steps of: illuminating said mask for forming an image of a pattern to be inspected at a predetermined imaging position from light passed through a phase-shifter deposited portion on said mask and light passed through a phase-shifter non-deposited portion on said mask respectively;

detecting first information corresponding to a light quantity at a position corresponding to said phase-shifter deposited portion within the inspection pattern image and second information corresponding to a light quantity at a position corresponding to a light quantity at a position corresponding to said phase-shifter non-deposited portion within the inspection pattern image at least one position relatively moved in an optical axis direction from said imaging position of said mask; and calculating a phase difference between said light passed through said phase-shifter deposited portion and said light passed through said phase-shifter non-deposited portion in accordance with a ratio between said first information and said second information wherein the detection of said first information and said second information is effected at each of a plurality of positions in said optical axis direction.

2. A method according to claim 1, further comprising the step of adjusting a numerical aperture of an illumination optical system used in said projecting step in a manner that a ratio of the numerical aperture of said illumination optical system to a numerical aperture of an imaging optical system used in said projecting step falls within a range from 0.1 to 0.3.

3. A method according to claim 1, further comprising the step of adjusting a numerical aperture of an imaging optical system in a manner that of said light passed through said mask the second and higher order diffracted beams are removed.

4. A method according to claim 1, further comprising the step of detecting peak intensities at said positions respectively corresponding to said phase-shifter deposited portion and said phase-shifter non-deposited portion within said inspection pattern image as said first information and said second information, respectively.

5. A method of inspecting a phase-shifted mask including at least one phase shifter adapted to change the phase of light and selectively deposited in correspondence to a desired pattern configuration, said method comprising the steps of:

illuminating said mask for forming an image of a pattern to be inspected at an imaging position from light passed through said phase-shifter deposited portion of said mask and the light passed through said phase-shifter deposited portion of said mask and the light passed through said phase-shifter non-deposited portion of said mask such that one of a +first-order diffracted beam is generated from the phase-shifter deposited portion at a different directional angle with respect to the light passed through said phase-shifter non-deposited portion;

detecting information corresponding to an intensity distribution of the image at said imaging position based upon said first order diffracted beam of said phase-shifter deposited portion; and calculating a phase difference between said light passed through said phase-shifter deposited portion and said light passed through said phase-shifter non-deposited portion in accordance with said information corresponding to said intensity distribution.

6. An apparatus for inspecting a phase shifted mask including at least one phase shifter adapted to change the phase of light and selectively deposited in correspondence to a desired pattern configuration, said apparatus comprising:

an illumination optical system for illuminating said mask;

an imaging optical system for forming an image of a pattern to be inspected at a predetermined imaging position by the light passed through a phase-shifter deposited portion on said mask and the light passed through a phase-shifter non-deposited portion on said mask respectively:

detecting means for detecting first information corresponding to a light quantity at a position corresponding to said phase-shifter deposited portion within said inspection pattern image and second information corresponding to a light quantity at a position corresponding to said phase-shifter non-deposited portion within said inspection pattern image;

moving means for moving said imaging position of said imaging optical system and said detecting means relatively in an optical axis direction a predetermined amount to shift the relative position of the projected image means for measuring said first and second information at said shifted position wherein the detection of said first information and said second information is effected at each of a plurality of positions in said optical axis direction; and means for calculating the light quantity difference as a result of said positional shift in order to determine the phase difference between the phase-shifter deposited portion and the phase-shifter non-deposited portion.

7. An apparatus according to claim 6, further comprising means for adjusting a numerical aperture of said illumination optical system in a manner that a ratio of the numerical aperture of said illumination optical system to a numerical aperture of said imaging optical system falls in a range from 0.1 to 0.3.

8. An apparatus according to claim 6, further comprising means for adjusting a numerical aperture of said imaging optical system in a manner that of the light transmitted through said mask the second and higher order diffracted beams are removed.

9. An apparatus according to claim 6, further comprising means for detecting peak intensities at said positions respectively corresponding to said phase-shifter deposited portion and said phase-shifter non-deposited portion within said inspection pattern image as said first information and second information, respectively.

10. An apparatus according to claim 6, further comprising processing means for calculating a phase difference between the light passed through said phase-shifter deposited portion and the light passed through said phase-shifter non-deposited portion in accordance with a ratio between said first and second information detected in a condition where the position of said detecting means relative to the imaging position of said imaging optical system has been moved a predetermined amount by said moving means.

11. An apparatus according to claim 6, wherein said inspection pattern includes a one-dimensional line and space pattern formed by the same manufacturing operation as at least part of an original drawing pattern on said mask at a different position thereof.

12. An apparatus according to claim 6, wherein said inspection pattern includes a plurality of said phase-shifter deposited portions and said phase-shifter non-deposited portions which are arranged alternately.

13. An apparatus according to claim 6, wherein said inspection pattern includes a plurality of said phase-shifter deposited portions and said phase-shifter non-deposited portions which are arranged alternately through the intermediary of light shielding means.

14. An apparatus according to claim 6, wherein said inspection pattern includes a plurality of said phase-shifter deposited portions and said phase-shifter non-deposited portions which are substantially equal in areas to each other.

15. An apparatus for inspecting a phase-shifted mask including at least one phase shifter adapted to change the phase of light and selectively deposited in correspondence to a desired pattern configuration, said apparatus comprising:

an illumination optical system for illuminating said mask;

an imaging optical system whereby an image of a pattern to be inspected which is formed by the light passed through said mask phase-shifter deposited portion and the light passed through said mask phase-shifter non-deposited portion is projected onto a predetermined imaging position;

light shielding means arranged in the vicinity of a Fourier transform plane within said imaging optical system in a manner that of the light transmitted through said inspection pattern beams other than a 0-order diffracted beam and ±first-order diffracted beams are intercepted, and that either one of said ±first-order diffracted beams is selectively intercepted; and pattern detecting means for photoelectrically detecting the image of said inspection pattern produced by said imaging optical system.

16. An apparatus according to claim 15, wherein said detecting means is movable in the direction of the optical axis of said imaging optical system, said detecting means further comprising:
control means responsive to a detection signal generated from said photoelectric detector to position said photoelectric detector at said imaging position; and
processing circuit means responsive to a detection signal generated from said control means when said photoelectric detector is positioned at said imaging position to calculate a phase difference between the light passed through said phase-shifter deposited portion and the light passed through said phase-shifter non-deposited portion.

17. An apparatus according to claim 15, wherein said light shielding means includes a light shielding member whereby of the light transmitted through said inspection pattern at least either one of said ±first-order diffracted beams is attenuated.

18. An apparatus according to claim 15, wherein said inspection pattern includes a one-dimensional line and space pattern formed by the same manufacturing operation as at least part of an original drawing pattern on said mask at a position different therefrom on said mask.

19. An apparatus according to claim 15, wherein said inspection pattern includes a plurality of said phase-shifter deposited portions and said phase-shifter non-deposited portions which are arranged alternately.

20. An apparatus according to claim 15, wherein said inspection pattern includes a plurality of said phase-shifter deposited portions and said phase-shifter non-deposited portions which are arranged alternately through the intermediary of light shielding means.

21. An apparatus according to claim 15, wherein an area ratio between said phase-shifter deposited portion and said phase-shifter non-deposited portion in said inspection pattern is in the range from 7:1 to 7:2 or 1:7 to 2:7.

22. An apparatus for inspecting a phase-shifted mask including at least one phase shifter adapted to change the phase of light and selectively deposited in correspondence to a desired pattern configuration, said apparatus comprising:
an illumination optical system for illuminating said mask;
an imaging optical system whereby an image of a pattern to be inspected which is formed by the light passed through said mask phase-shifter deposited portion and the light passed through said mask phase-shifter non-deposited portion is projected onto a predetermined imaging position;
beam deflecting means for determining a direction of incidence of the illuminating light from said illumination optical system on said mask in a manner that said illuminating light falls at a predetermined angle of incidence on said mask, and that of the light transmitted through said inspection pattern a 0-order diffracted beam and either one of ±first-order diffracted beams are respectively passed through a Fourier transform plane within said imaging optical system at positions which are substantially symmetric with respect to an optical axis of said imaging optical system; and
pattern detecting means arranged at or near said imaging position for photoelectrically detecting the image of said inspection pattern produced by said imaging optical system.

23. An apparatus according to claim 22, wherein said pattern detecting means comprises:
a photoelectric detector for detecting said 0-order diffracted beam and either one of said ±first-order diffracted beams; and
a processing circuit responsive to a detection signal generated from said photoelectric detector to calculate a phase difference between the light passed through said phase-shifter deposited portion and the light passed through said phase-shifter non-deposited portion.

24. An apparatus according to claim 22, wherein said imaging optical system includes a spatial filter arranged in the vicinity of a Fourier transform plane of said imaging optical system to intercept the other beams than said 0-order diffracted beam and either one of said ±first-order diffracted beams which are transmitted through said inspection pattern.

25. An apparatus according to claim 22, wherein said imaging optical system includes light shielding means for attenuating at least one of said 0-order diffracted beam and said + or −first-order diffracted beam which are transmitted through said inspection pattern.

26. An apparatus according to claim 22, wherein said inspection pattern includes a one-dimentional line and space pattern formed by the same manufacturing operation as at least part of an original drawing pattern on said mask at a position different therefrom on said mask.

27. An apparatus according to claim 22, wherein said inspection pattern comprises a plurality of said phase-shifter deposited portions and said phase-shifter non-deposited portions which are arranged alternately.

28. An apparatus according to claim 22, wherein said inspection pattern comprises a plurality of said phase-shifter deposited portions and said phase-shifter non-deposited portions which are alternately arranged through the intermediary of light shielding means.

29. An apparatus according to claim 23, wherein an area ratio between said phase-shifter deposited poriton and said phase-shifter non-deposited portion in said inspection pattern is in the range from 7:1 to 7:2 or 1:7 to 2:7.

* * * * *